United States Patent
Matsumura

(10) Patent No.: US 8,845,538 B2
(45) Date of Patent: Sep. 30, 2014

(54) ULTRASONIC DIAGNOSTIC APPARATUS

(75) Inventor: Takeshi Matsumura, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 70 days.

(21) Appl. No.: 12/989,546

(22) PCT Filed: Apr. 14, 2009

(86) PCT No.: PCT/JP2009/057471
§ 371 (c)(1),
(2), (4) Date: Oct. 25, 2010

(87) PCT Pub. No.: WO2009/131029
PCT Pub. Date: Oct. 29, 2009

(65) Prior Publication Data
US 2011/0040187 A1    Feb. 17, 2011

(30) Foreign Application Priority Data
Apr. 25, 2008   (JP) .................................. 2008-116313

(51) Int. Cl.
| A61B 8/00 | (2006.01) |
| A61B 5/00 | (2006.01) |
| A61B 8/08 | (2006.01) |
| A61B 8/13 | (2006.01) |
| A61B 8/06 | (2006.01) |

(52) U.S. Cl.
CPC . *A61B 8/485* (2013.01); *A61B 8/13* (2013.01); *A61B 8/06* (2013.01); *A61B 5/6843* (2013.01); *A61B 8/488* (2013.01); *A61B 8/4281* (2013.01)
USPC ............ 600/443; 600/437; 600/447; 600/459

(58) Field of Classification Search
CPC .... A61B 5/6843; A61B 8/488; A61B 8/4281; A61B 8/485
See application file for complete search history.

(56) References Cited

U.S. PATENT DOCUMENTS

| 6,003,378 A * | 12/1999 | Scherr et al. ..................... 73/703 |
| 2002/0103432 A1 | 8/2002 | Kawchuk |

(Continued)

FOREIGN PATENT DOCUMENTS

| EP | 1 762 180 A1 | 3/2007 | |
| EP | 1762180 A1 * | 3/2007 | ............... A61B 8/00 |

(Continued)

OTHER PUBLICATIONS

Talbi et al., Surface Acoustic Wave Pressure Sensor, Ferroelectrics, 2002, vol. 273, pp. 53-58.*

(Continued)

*Primary Examiner* — Long V. Le
*Assistant Examiner* — Bo J Peng
(74) *Attorney, Agent, or Firm* — Antonelli, Terry, Stout & Kraus, LLP.

(57) ABSTRACT

The invention was made to simplify the operation relating to the detection of an absolute pressure applied to a test body by an ultrasonic probe and thereby to enhance usability. The fact that an elastic coupler has been attached to the ultrasonic wave transmitter/receiver surface and the fact that the elastic coupler is in an initial state with no pressure are detected (S2, S3), an initial thickness of the elastic coupler in the initial state is obtained (S6), the fact that the elastic coupler is in the pressurized state is detected based on the disappearance of a multiple echo which is included in an RF signal and caused due to the elastic coupler, the thickness of the elastic coupler in the pressurized state is obtained by detecting the boundary between the test body and the elastic coupler in the pressurized state, the thickness change is obtained based on the thickness in the pressurized state and the initial thickness (S7), and the absolute pressure applied to the test object is evaluated based on the thickness change and the pre-set elasticity property of the elastic coupler (S8).

17 Claims, 15 Drawing Sheets

(56) References Cited

U.S. PATENT DOCUMENTS

| | | |
|---|---|---|
| 2002/0146927 A1* | 10/2002 | Uchibori et al. ............... 439/364 |
| 2005/0154308 A1 | 7/2005 | Quistgaard et al. |
| 2005/0203398 A1 | 9/2005 | Sandrin et al. |
| 2008/0027328 A1 | 1/2008 | Klopotek et al. |

FOREIGN PATENT DOCUMENTS

| | | | | |
|---|---|---|---|---|
| JP | 2005-066041 | | 3/2005 | |
| JP | 2005-066041 A | | 3/2005 | |
| JP | 2005066041 A | * | 3/2005 | ............... A61B 8/08 |
| JP | 2006-247203 | | 9/2006 | |
| WO | WO 2005/107599 A1 | | 11/2005 | |
| WO | WO 2005/120358 A1 | | 12/2005 | |
| WO | WO 2006/121031 A1 | | 11/2006 | |
| WO | WO 2007/086373 A1 | | 8/2007 | |
| WO | WO 2008016022 | * | 2/2008 | ............... A61B 8/08 |

OTHER PUBLICATIONS

Lee et al., Surface Acoustic Wave Based Pressure Sensor with Ground Shielding over Cavity on 410 YX LiNbO3, Japanese Journal of Applied Physics, vol. 45, No. 7, 2006, pp. 5974-5980.*

* cited by examiner

ULTRASONIC DIAGNOSTIC APPARATUS

TECHNICAL FIELD

The present invention relates to an ultrasonic diagnostic apparatus, and particularly to an ultrasonic diagnostic apparatus with a function for evaluating a pressure to be applied to a test object by an ultrasonic probe at the time of a test such as a diagnosis by a tomographic image (B mode image) or elasticity information of a body tissue of a test object, or a bloodstream diagnosis by Doppler measurement or a color flow mode (CFM).

BACKGROUND ART

Generally, an ultrasonic diagnostic apparatus is for performing a diagnosis such that ultrasonic waves are transmitted into a body of a test object from an ultrasonic probe (hereinafter, simply referred to as a probe), a reflected echo signal of the ultrasonic waves which have been reflected from the inside of the body is received by the probe, and an image or the like which is suitable for the test of a tissue, a function, or the like inside the body is created based on the received reflected echo signal (RF signal).

In such an ultrasonic diagnostic apparatus, for the test by a B mode image, it is preferable to obtain an image with a high image quality by placing the probe on the test body with a relatively strong force, pressing and deforming the body tissue so that the deep tissue can be closer to the probe, and imaging the tissue since the ultrasonic waves attenuate in the course of the propagation inside the body tissue.

On the other hand, in the bloodstream test such as the Doppler measurement or the CFM, since it is not possible to obtain correct information on the bloodstream because the cross-section of the blood vessel is deformed when the probe is placed on and pressed against the body tissue with an excessively strong force, it is preferable to perform the test with the pressurizing state which is gentler than that at the time of the B mode diagnosis.

In addition, since the body tissue has a nonlinearity in which the hardness of the tissue changes in accordance with the strength of the pressurizing even in the test by elastography for creating an image of elasticity information regarding the hardness or the softness of the body tissue, it is important to perform a diagnosis based on an elasticity image obtained under a pressurizing state with a constant pressure.

That is, although it has been recognized that a suitable pressurizing state (pressure) is different depending on the testing method, it is required that more experiences are accumulated until suitable pressurizing states are learned for all kinds of diagnoses. In addition, depending on a test, for example, a testing process frequently occurs in which a tomographic image of a site of interest is imaged and stored in the B mode and the B mode is then directly shifted to the Doppler measurement for obtaining the bloodstream information of the same cross-section. In the case of such a testing process, there is a concern that correct information on the bloodstream cannot be obtained as described above if a Doppler image is obtained while a relatively strong pressurizing state suitable for obtaining the B mode image is being maintained. That is, there is a concern that a test is performed while an unsuitable pressurizing state is being maintained in the respective testing methods or at the time of transferring between testing methods, which hinders a prompt appropriate diagnosis.

Accordingly, a method of measuring an actual pressure to be applied to the body tissue of the test object, that is, an absolute pressure to be applied to the body tissue (hereinafter, simply referred to as an absolute pressure) is disclosed in Patent Literature 1, for example. According to this method, an elastic coupler which is a deformable unit for the pressure measurement is attached to an ultrasonic wave transmitter/receiver surface of a probe, a pressure is applied to a test body by the probe via the elastic coupler, and an absolute pressure is obtained based on the deformation of the elastic coupler at that time.

Thus, according to the method of evaluating the pressurizing state disclosed in Patent Literature 1, it is possible to obtain the elasticity information on the hardness or softness of the body tissue by measuring absolute pressure applied to the test body, for example.

CITATION LIST

Patent Literature

PTL 1: JP-A-2005-66041

SUMMARY OF INVENTION

Problem to be Solved by the Invention

It is difficult to cope with the detection of absolute pressure, which widely ranges, only with one kind of elastic coupler since suitable pressurizing force differs significantly depending on a testing method, depth of the site of interest, and the like. Thus, it is preferable to prepare a plurality of elastic couplers with different elastic properties in accordance with the suitable range of the absolute pressure and to replace the elastic coupler depending on the testing method, the depth of the site of interest, and the like.

According to the technique of Patent Literature 1, however, an operator is required to input an initial thickness $D(0)$ and an elastic property of the elastic coupler and thereby to perform an initial setting every time the elastic coupler is replaced. There is a problem that the burden on the operator becomes larger since the operation of the initial setting becomes complicated and the test needs to be executed again when the initial setting fails.

The problem to be solved by the invention is to simplify the operation relating to the detection of the absolute pressure applied to the test body by the ultrasonic probe and thereby to enhance usability.

Means for Solving the Problem

In order to solve the above problem, the invention provides an ultrasonic diagnostic apparatus including an ultrasonic probe for transmitting and receiving ultrasonic waves while being in contact with a test body, a transmitting unit for transmitting the ultrasonic waves to the ultrasonic probe, a receiving unit for receiving and processing an RF signal which is a reflected echo signal received by the ultrasonic probe, an image creating unit for creating an ultrasonic image based on the RF signal output from the receiving unit, a display unit for displaying the ultrasonic image created by the image creating unit, and a control unit for controlling the transmitting means and the receiving means, and including a pressurizing-state evaluation unit for evaluating the pressure applied to the test body based on the deformation of an elastic coupler which has been attached to an ultrasonic wave transmitter/receiver surface of the ultrasonic probe. Here, the pressurizing-state evaluation unit includes an initialization process unit for detecting the position of an exposure surface of the elastic coupler in an initial state in which the elastic coupler is not pressurized and obtaining the initial thickness, and a coupler pressurization evaluation unit for obtaining the thickness of the elastic coupler by detecting the boundary between the elastic coupler and the test body, obtaining the thickness change based on the thus obtained thickness and the initial thickness, and evaluating the pressure based on the thickness change and an elasticity property of the elastic coupler.

(Initialization Process Unit)

The initialization process unit detects that the elastic coupler is in an initial state with no pressure being applied based on the RF signal, detects the position of the exposure surface of the elastic coupler based on the RE signal in the initial state of the elastic coupler, and obtains the initial thickness. With this configuration, the pressurizing-state evaluation unit can automatically recognize the attachment and the detachment of the elastic coupler even when the elastic coupler is replaced or detached in accordance with the testing method, the depth of the site of interest, or the like, and it is possible to automatically obtain the initial thickness of the elastic coupler.

Firstly, in the first example for detecting that the elastic coupler is in the initial state with no pressure being applied, it is determined that the elastic coupler has been attached based on the change in intensity where the RF signal changes so as to exceed a pre-set threshold value. In the second example, any one of the RF signal and the illuminance data of the ultrasonic image created based on the RF signal is received, and the attachment of the elastic coupler is detected based on the frequency of the multiple echo where the intensity of the received RF signal or the illuminance of the ultrasonic image changes so as to exceed a pre-set threshold value.

That is, since an acoustic lens provided on the ultrasonic wave receiver surface of the ultrasonic probe is exposed in the air when the elastic coupler is not attached, the multiple echo reflected by the exposure surface is included in the RF signal, and the frequency correlates with the thickness of the acoustic lens. On the other hand, if the elastic coupler is attached, the multiple echo due to the acoustic lens disappears. Thus, it is possible to detect the attachment of the elastic coupler based on the existence of the multiple echo due to the acoustic lens. In addition, since the multiple echo of the frequency corresponding to the thickness of the elastic coupler, which is reflected by the exposure surface of the elastic coupler, is included in the RF signal when the elastic coupler is attached and the surface of the elastic coupler on the test body side is exposed in the air, it is possible to detect the attachment of the elastic coupler based on the existence of the multiple echo due to the elastic coupler.

Moreover, in the third example for detecting that the elastic coupler is in the initial state with no pressure being applied, the attachment of the elastic coupler is detected by forming a layer of ultrasonic scattering bodies formed inside the plate-shaped unit of the elastic coupler formed from a gel-like material, receiving any one of the RF signal and the illuminance data of the ultrasonic image created based on the RF signal, and detecting the ultrasonic scattering bodies based on the intensity distribution of the received RF signal or the illuminance distribution of the ultrasonic image. In the fourth example, the elastic coupler is attached to the ultrasonic probe via an attachment tool, the attachment tool includes a locking protrusion which is detachably locked in a locking portion formed in a case of the ultrasonic probe, and the attachment of the elastic coupler is detected based on a signal output from an attachment sensor which operates in the state in which the locking protrusion is locked in the locking portion of the ultrasonic probe.

Next, in the first example for obtaining the initial thickness of the elastic coupler, the exposure surface of the elastic coupler is detected in the state in which the elastic coupler is attached, based on the time from a point in time at which an ultrasonic signal is output from the transmitting unit to the ultrasonic probe to a point in time at which the intensity of the RF signal corresponding to the ultrasonic signal or the illuminance of the ultrasonic image exceeds a pre-set threshold value for the first time, and the initial thickness of the elastic coupler is detected. In the second example, any one of the RF signal and the illuminance data of the ultrasonic image created based on the RF signal is received, the frequency of the multiple echo where the intensity of the received RF signal or the illuminance of the ultrasonic image changes so as to exceed the pre-set threshold value is detected, and the initial thickness of the elastic coupler is obtained based on the frequency and the speed of sound.

(Coupler Pressurization Evaluation Unit)

The coupler pressurization evaluation unit obtains the thickness of the elastic coupler by detecting the boundary between the elastic coupler and the test body based on the RF signal, obtains the thickness change based on the above thickness and the initial thickness, and obtains the absolute pressure applied to the test body based on the thickness change and the elasticity property of the elastic coupler, which was set in advance.

Here, in regard to whether or not the elastic coupler is in the pressurized state, it is possible to detect that the elastic coupler is in the pressurized state by receiving any one of the RF signal and the illuminance data of the ultrasonic image created based on the RF signal, based on the fact that the intensity of the received RF signal or the illuminance of the ultrasonic image does not periodically change so as to exceed the pre-set threshold value, that is, the fact that the above-mentioned multiple echo is not detected.

Next, as for the calculation of the absolute pressure applied to the test body, the thickness of the elastic coupler in the pressurized state is obtained by receiving any one of the RF signal corresponding to the ultrasonic signal output from the transmitting unit to the ultrasonic probe or the illuminance data of the ultrasonic image created based on the RF signal when the elastic coupler is in the pressurized state and detecting the contact surface between the elastic coupler and the test body based on the time which was required for the intensity of the received RF signal or the illuminance of the ultrasonic image to exceed the pre-set threshold value for the first time. That is, the intensity of the RF signal corresponding to the ultrasonic waves output from the ultrasonic probe changes significantly at the boundary surface (contact surface) between the elastic coupler and the test body. For this reason, the time from the point in time at which the ultrasonic waves are transmitted from the ultrasonic probe to the point in time at which the RF signal exceeds the threshold value is detected, half of the time is multiplied by the speed of sound, and thereby the thickness of the elastic coupler is obtained. The thickness change is obtained by comparing the thus obtained thickness and the initial thickness, and the absolute pressure applied to the test body is calculated based on the thickness change and the elasticity property of the elastic coupler.

Here, it is possible that the elasticity property (for example, a elastic modulus) of the elastic coupler is stored in advance in a storage unit such as a memory and read from the memory by the operator by inputting the identification sign or the like of the type of the elastic coupler via an input unit at the time of the replacement or the attachment. In addition, the value obtained by being automatically measured by the above-mentioned initialization process unit is used as the initial thickness.

The coupler pressurization evaluation unit receives the RF signal frame data output from the receiving unit in an initial state and the RF signal frame data output from the receiving unit in the measurement of a pressurized state, obtains distortion by obtaining displacement of a measurement point within the elastic coupler based on the pair of RF signal frame data, and obtains the absolute pressure applied to the test body based on the thus obtained distortion and the elasticity property which has been set corresponding to the type of the elastic coupler.

The coupler pressurization evaluation unit sequentially receives a pair of RF signal frame data which was obtained at different timings and output from the receiving unit while including the initial state, obtains distortions by obtaining displacement of a measurement point within the elastic coupler based on the pair of RF signal frame data, sums up the distortions from the initial state to the pressurized state, and obtains an absolute pressure applied to the test body based on the distortion summed-up value and the elasticity property. That is, the coupler pressurization evaluation unit temporally repeats the process for obtaining the distortion by obtaining the displacement of the measurement point within the elastic coupler, from the initial state, obtains the distortion summed-up value by summing up the distortion changes which have been thus obtained by the repetition, and calculates the absolute pressure at the time of the summing-up, which is applied to the test body, based on the obtained distortion summed-up value and the elasticity property which was set corresponding to the type of the elastic coupler.

In this case, it is preferable that the elastic coupler be formed into a plate-shaped unit from a gel-like material and is obtained by diffusing and mixing ultrasonic scattering bodies inside the plate-shaped unit. With such a configuration, it is possible to increase the RF signal from the measurement point within the elastic coupler and thereby to enhance the accuracy in detection of the displacement and the distortion and in evaluation of the absolute pressure.

In the invention, it is preferable that the pressurizing-state evaluation unit displays at least one of the numerical value of the obtained absolute value, a graph of a temporal change, a bar chart, and the like while aligning with the ultrasonic image displayed on the display unit. With such a configuration, it is possible to monitor the pressurizing state in real time, evaluate whether or not the pressurizing state is suitable for various test methods, and thereby to support the test in an appropriate pressurizing state regardless of the extent of experience of the operator.

Advantageous Effects of Invention

According to the invention, it is possible to simplify the operation relating to the detection of absolute pressure to be applied to a test body by an ultrasonic probe and thereby to enhance usability.

REFERENCE SIGNS LIST

1: Probe
2: Transmitting Circuit
3: Receiving Circuit
8: Switch Adder
9: Image Display
10: RF Signal Frame Data Selection Unit
11: Displacement Calculator
12: Elasticity Calculator
13: Elasticity Data Process Unit
19: Control Interface Unit
20: Elastic Coupler
30, 50: Pressurizing-State Evaluation Unit
31: Coupler Attachment Detector
33, 52: Pressurizing-State Calculator
34: Initialization Process Unit
35: Pressurized-State Detector
36, 54: Coupler Pressurization Evaluation Unit
37, 55: Pressure Converter
38: Pressurizing-State Image Constructing Unit
51: Coupler ID Identification Unit
53: Coupler Database

MODES FOR CARRYING OUT THE INVENTION

Hereinafter, a description will be made of the examples of the ultrasonic diagnostic apparatus according to the invention with reference to the drawings.

EXAMPLE 1

Figure 1:
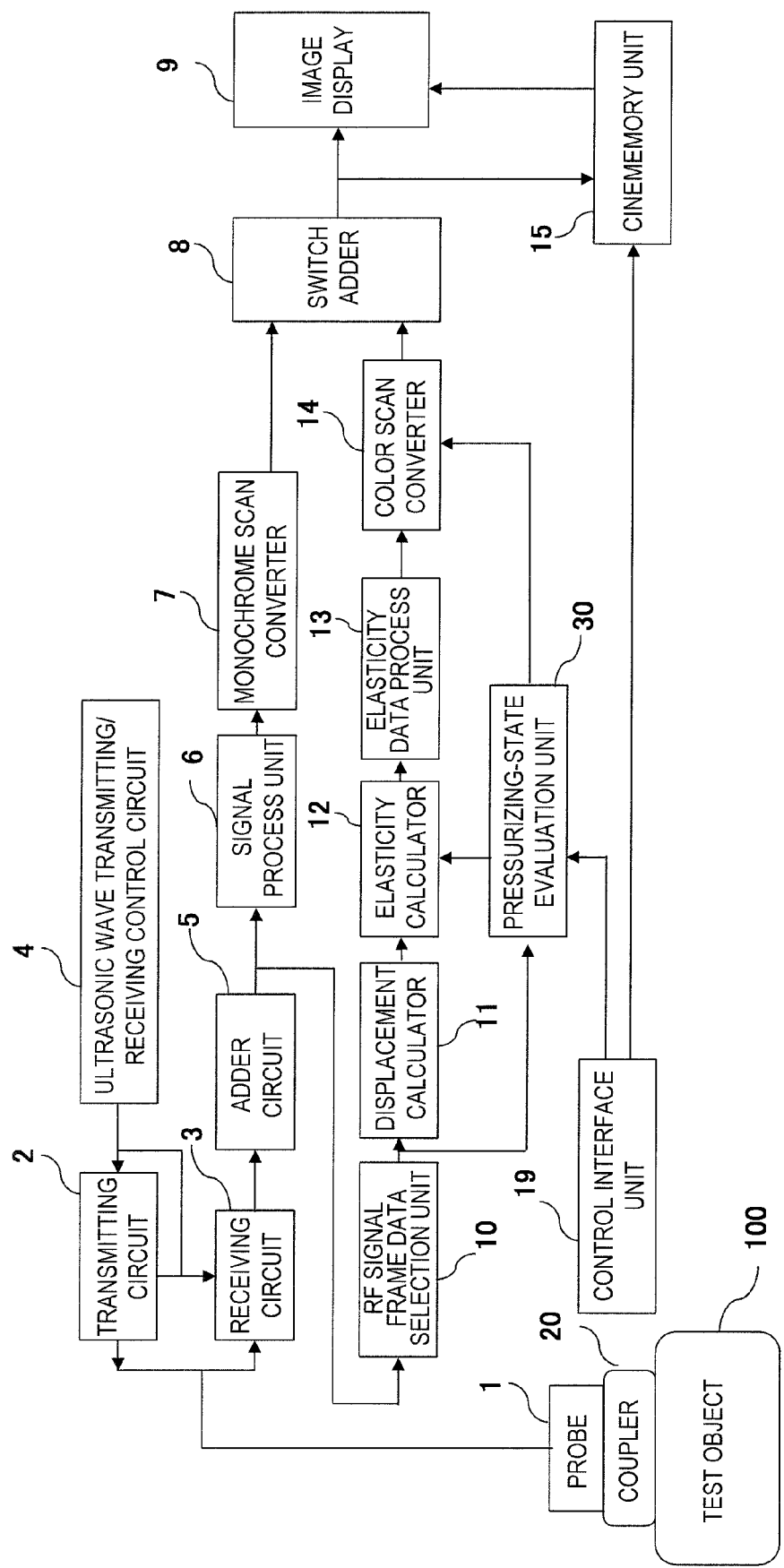
FIG. 1 is a block configuration diagram of an ultrasonic diagnostic apparatus of Example 1 of the invention.
Figure 3:
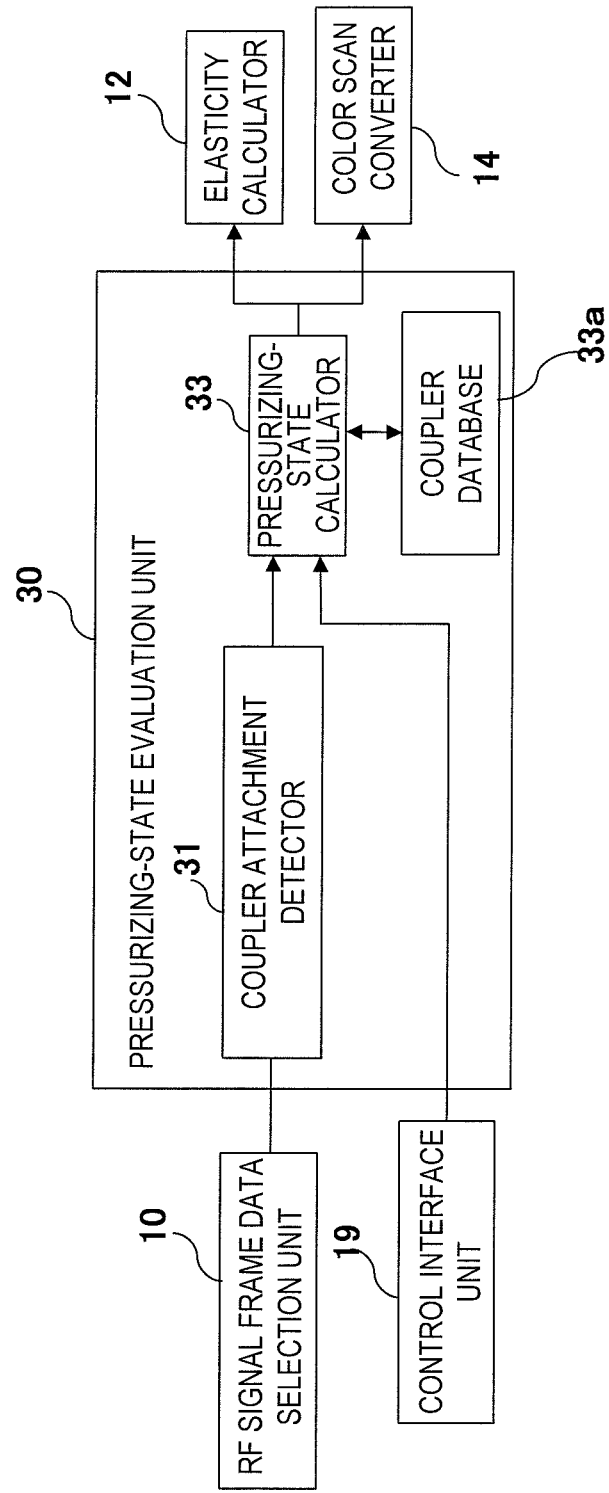
FIG. 3 is a block configuration diagram illustrating a detailed configuration of a pressurizing-state evaluation unit of Example 1.
Figure 4:
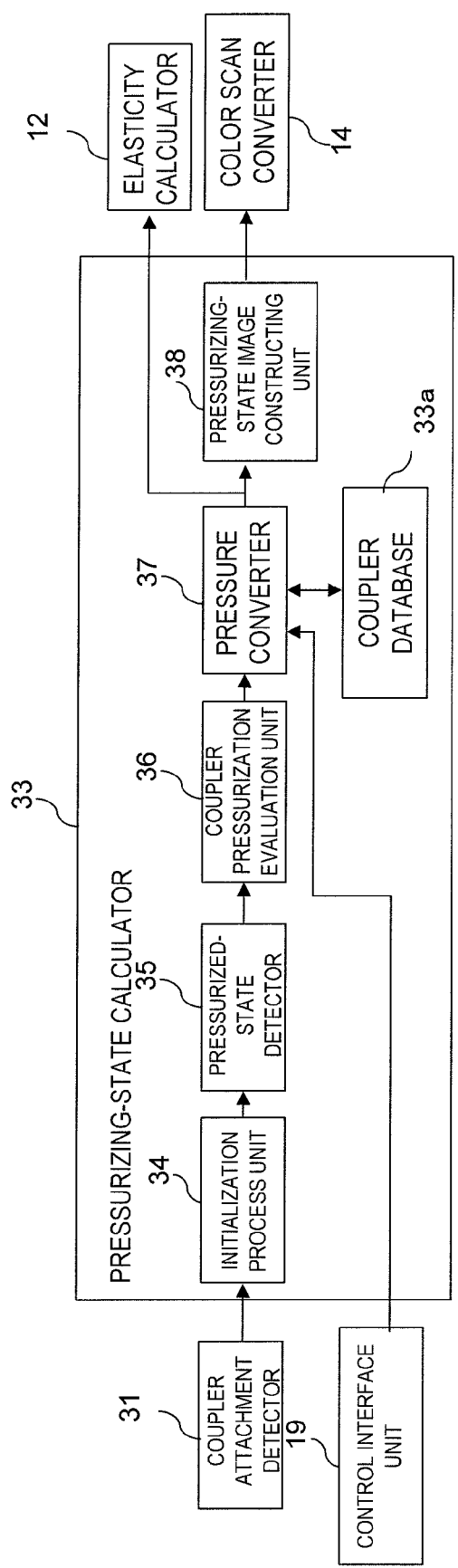
FIG. 4 is a block configuration diagram illustrating a detailed configuration of a pressurizing-state calculator of Example 1.

FIG. 1 shows a functional block configuration diagram of an ultrasonic diagnostic apparatus according to an example of the invention. FIG. 2(A) is a perspective view of an elastic coupler to be applied to this example, and FIG. 2(B) shows a sectional view of the elastic coupler attached to an ultrasonic probe via an attachment tool. FIGS. 3 and 4 are detailed functional block configuration diagrams of a pressurizing-state evaluation unit of this example.

As shown in FIG. 1, the ultrasonic diagnostic apparatus of this example is for obtaining a tomographic image of a site as a diagnostic target of the test object with the use of ultrasonic waves and displaying an elasticity image representing the hardness or the softness of the body tissue. As shown in the same drawing, an ultrasonic probe (hereinafter, simply referred to as a probe) 1 is electrically connected to a transmitting circuit 2 and a receiving circuit 3. As is well known, the probe 1 is a generation source of the ultrasonic waves and is formed such that a plurality of oscillators for receiving the waves of reflected echo is arranged in a strip shape. Each oscillator generally has a function of converting an ultrasonic signal of input pulse waves or continuous waves into ultrasonic waves and emitting the ultrasonic waves and a function of converting reflected echo emitted from the inside of a test object 100 into a reflected echo signal which is an electric signal and outputting the reflected echo signal.

The transmitting circuit 2 is configured such that the transmitting circuit 2 and the receiving circuit 3 are cooperatively controlled by an ultrasonic wave transmitting/receiving control circuit 4. The ultrasonic wave transmitting/receiving control circuit 4 is for controlling the timing at which the ultrasonic waves are transmitted and received, controls the transmitting circuit 2 to radiate an ultrasonic wave transmitting beam suitable for the targeted ultrasonic examination into the test object 100 from the probe 1 in response to the command input from a control interface unit 19, and controls the receiving circuit 3 to receive a desired ultrasonic wave receiving beam from the probe 1. The ultrasonic wave transmitting/receiving control circuit 4 of this example controls the transmitting circuit 2 and the receiving circuit 3 to scan the ultrasonic wave transmitting beam along a cross-sectional plane so as to form the ultrasonic wave transmitting beam and the ultrasonic wave receiving beam suitable for the measurement of a B mode tomographic image.

The receiving circuit 3 amplifies the reflected echo signal, which has been received by the probe 1, at a predetermined gain. The reflected echo signals, the number of which corresponds to the number of the amplified oscillators, is input to the adder circuit 5. The adder circuit 5 adds the total of the phases of the plurality of reflected echo signals which have been amplified by the receiving circuit 3 and creates RF signal frame data corresponding to the cross-sectional plane.

A signal process unit 6 inputs the RF signal frame data output from the adder circuit 5 and performs various kinds of signal process such as gain correction, log correction, wave detection, contour enhancement, and filter process to create image data. A monochrome scan converter 7 is configured to include cross-section scanning means for obtaining the image data, which has been output from the signal process unit 6, in an ultrasonic frequency and reading the image data in a frequency based on the television scheme for displaying this ultrasonic image and means for controlling the system including, for example, an A/D converter for converting the image data from the signal process unit 6 into a digital signal, a plurality of frame memories for storing the image data which has been converted into a digital signal by this A/D converter in a time series manner, a controller for controlling these operations, and the like. The image data for a B mode image, for example, in a time series manner, which has been created by the monochrome scan converter 7 is output to an image display 9 via a switch adder 8. The image display 9 includes a D/A converter for converting the image data output from the monochrome scan converter 7 into an analog signal and a color television monitor for displaying the analog video signal output from this D/A converter as an image.

Next, a description will be made of the process for creating an elasticity image and causing the image display 9 to display the elasticity image according to this example. Generally, the deformation of a body tissue due to a pressure (stress) applied to the body tissue of the site as a diagnostic target by pressurizing the test object 100 with the probe 1 is used in order to create the elasticity image. That is, a degree of the deformation differs depending on the elasticity, which is the hardness or the softness of the body tissue, even when the same stress acts on the body tissue. Thus, the elasticity image, with which a normal site and a site of disease can be identified, is created by performing the ultrasonic wave transmitting/receiving with the probe 1 and obtaining the degree of the deformation of the tissue with the use of the RF signal frame data corresponding to a pair of B mode images at the time of pressurizing the test object 100 by the probe 1 with different pressures.

In this example, the RF signal frame data created by the adder circuit 5 is input to the RF signal frame data selection unit 10. The RF signal frame data selection unit 10 sequentially accumulates the RF signal frame data, which is sequentially output from the adder circuit 5, in the frame memory. Then, in response to the command from the control unit which is not illustrated, the RF signal frame data selection unit 10 selects, for example, the latest RF signal frame data and one piece of RF signal frame data from among the plural pieces of RF signal frame data in the past and outputs a pair of RF signal frame data obtained at different timings to a displacement calculator 11. In addition, the RF signals may be signals with forms of I and Q signals which have been subjected to sign demodulation.

The displacement calculator 11 executes a one-dimensional or two-dimensional correlation process with respect to the pair of RF signal frame data output from the RF signal frame data selection unit 10 and calculates the displacement (or the displacement vector) of a plurality of measurement points i and j which have been set respectively in the scanning direction and in the depth direction of the ultrasonic beam of the RF signal frame data. The calculated displacement data at the plurality of measurement points is output as displacement frame data to an elasticity calculator 12. In addition, as a method of the displacement calculation, known methods including the block matching method and the gradient method can be used as disclosed in Patent Literature 1, for example, in addition to the correlation process. The block matching method is a method in which a marked block including a plurality of pixels around a pixel at the marked measurement point is set, the block with the image information which closely resembles that of the marked block is searched while moving with respect to the frame before the displacement, and the displacement is regarded as from the position of the block which most closely resembles to the current position.

The elasticity calculator 12 calculates the distortion of the respective measurement points by spatially differentiating the displacement of the respective measurement points with the use of the input displacement frame data as is already known. The distortion frame data is created based on the distortion at the respective measurement points which have been obtained by the calculation. Furthermore, the elasticity calculator 12 calculates elastic modulus (for example, Young's modulus) at the respective measurement points by a known method based on the distortion at the respective measurement points obtained by the calculation and based on the absolute pressure (stress), which is given from the pressurizing-state evaluation unit 30, which will be described later, and which is acting on the respective measurement points i and j. The elastic modulus frame data is created based on the elastic modulus at the respective measurement points obtained by the calculation and is output to the elasticity data process unit 13. The elasticity data process unit 13 performs various kinds of image process such as smoothing process in a frame, contrast optimization process, and smoothing process in a time axis direction between frames with respect to the elasticity frame data of the elastic modulus or the distortion created by the elasticity calculator 12 and outputs the processed data to a color scan converter 14.

The color scan converter 14 creates elasticity image data by adding color phase information of red, green, blue, or the like to the pixel corresponding to each measurement point based on the elasticity frame data output from the elasticity data process unit 13. For example, in the distortion frame data output from the elasticity data process unit 13, the pixel for which large distortion has been measured is converted into a red code within the elasticity image data, and on the other hand, the pixel for which small distortion has been measured is converted into a blue code within the elasticity image data. The elasticity image data is created by adding color phase information to the respective pixels in the case of the elastic modulus frame data as well. In addition, it is also possible to add an illuminance level corresponding to the size of the distortion or the like with the use of the monochrome scan converter instead of the color scan converter 14.

The elasticity image data created by the color scan converter 14 is output to a switch adder 8. The switch adder 8 input the monochrome tomographic image data output from the monochrome scan converter 7 and the color elasticity image data output from the color scan converter 14, adds or shifts both the images in response to the input command, and outputs the added or shifted images to the image display 9. Specifically, it is possible to cause the image display 9 to switch and display only the monochrome tomographic image data, only the color elasticity image data, or both the images in an aligned manner. In addition, it is possible to switch the output image in response to the input command, for example, by causing the image display 9 to perform the additive synthesis on both pieces of image data, that is, to create half-transparent overlapping images and to output and display the obtained image.

In addition, it is possible to cause a cinememory unit 15 to store the image data output from the switch adder 8. The image data stored in the cinememory unit 15 is displayed on the image display 9 in response to the command.

Next, a description will be made of the detailed configurations of the elastic coupler 20 and the pressurizing-state evaluation unit 30, which are the characteristic units of this example.

[Elastic Coupler 20]

Figure 2:
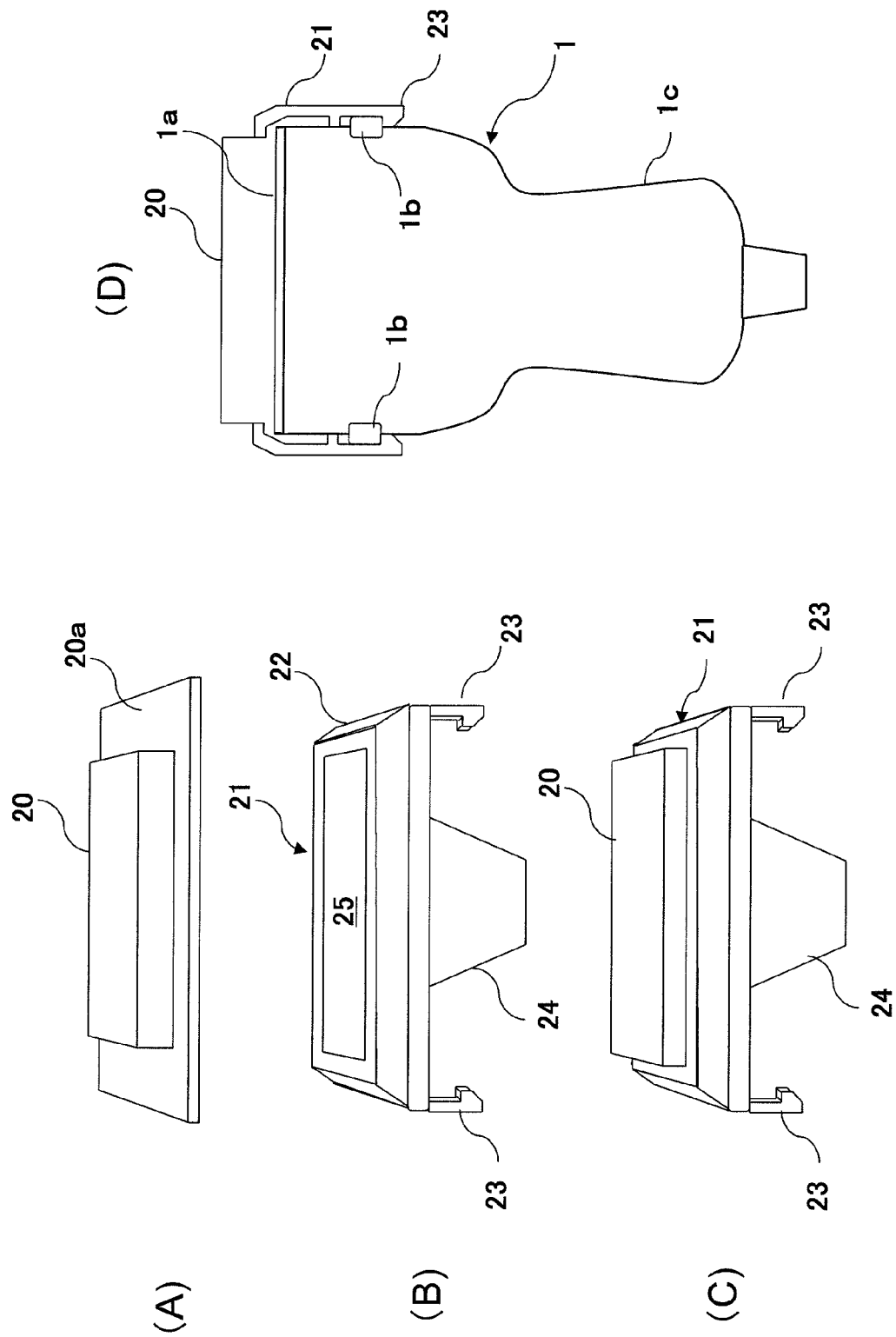
FIG. 2 is a configuration diagram of an example of an elastic coupler to be used in the ultrasonic diagnostic apparatus of Example 1.

FIG. 2 shows an example of the elastic coupler 20. The elastic coupler 20 is formed to have a brim portion 20a around one surface of a plate-shaped unit which has been formed from a gel-like material as shown in the perspective view of FIG. 2(A). The gel-like material forming the elastic coupler, in which an ultrasonic attenuation is small similarly to an acoustic combining material, an acoustic lens material, and the like, and the sonic speed and the acoustic impedance are close to those in the body, and which has an excellent acoustic combining property with the body, is preferable as described in Patent Literature 1. In addition, it is preferable to use a material which is excellent in a shape retention property, flexibility, appropriate elasticity, and a shape restoration property. Particularly, it is preferable to use a material which does not generate a gap even when it comes in contact with a contact surface with the ultrasonic wave transmitter/receiver surface 1a and with a part with unevenness such as a body surface even in the case where the elastic coupler 20 is attached to the ultrasonic wave transmitter/receiver surface 1a of the probe 1. That is, if a gap is generated between the ultrasonic wave transmitter/receiver surface 1a and the body surface, the ultrasonic waves irradiated from the probe 1 are reflected at the boundary of the air at the gap and becomes noise in the ultrasonic image. For example, it is possible to use aqueous gel (hydrogel) constituted by water and aqueous polymers such as gelatin, agar, oil gel, acrylamide, or polyvinyl alcohol, polyurethane, oil gel obtained by cross-linking and molding a composition containing rubber and oily component, and rubber obtained by molding and cross-linking a composition containing rubber with a low molecular weight blended as plasticizer into crude rubber.

The elastic coupler 20 formed in this manner is attached to the attachment tool 21 shown in FIG. 2(B) in the manner as shown in FIG. 2(C) and used while being attached to the ultrasonic wave transmitter/receiver surface 1a of the probe 1 as shown in FIG. 2(D). That is, the attachment tool 21 includes a head portion 22 with a truncated pyramid shape which has been formed by resin or the like to have a cup shape, a pair of locking claws 23 formed at the side edge which the bottom part of the head portion 22 faces, and a pair of gripped pieces 24 at the opposite side edge. The top surface of the head portion 22 is formed with an opening 25 into which the elastic coupler 20 is inserted. The elastic coupler 20 is inserted into the opening 25 from the bottom part of the attachment tool 21, and the brim portion 20a of the elastic coupler 20 is bent toward the inside of the cup-shaped head portion 22 and assembled therein. The attachment tool 21 to which the elastic coupler 20 has been attached is attached to the ultrasonic wave transmitter/receiver surface 1a of the probe 1 with jelly or the like interposed therebetween so as not to generate a gap between the lower surface of the elastic coupler 20 and the contact surface with the ultrasonic wave transmitter/receiver surface 1a as shown in FIG. 2(D). At this time, the locking claws 23 of the attachment tool 21 are hooked to the locking portion 1b provided on the side surface of the probe 1 and firmly fixed.

The ultrasonic examination is performed while gripping the gripped portions 1c of the probe 1 to which the elastic coupler 20 has been attached in the above manner and placing the exposure surface of the elastic coupler 20 on the body surface of the test object 100.

[Pressurizing-State Evaluation Unit]

The pressurizing-state evaluation unit 30 is configured to have a coupler attachment detector 31 for detecting whether or not the elastic coupler 20 has been attached based on the intensity change in the RF signal of the RF signal frame data output from the RF signal frame data selection unit 10, a pressurizing-state calculator 33 which is started based on the attachment detection signal of the elastic coupler 20 and evaluates the absolute pressure applied to the test object 100 based on the RF signal frame data, and a coupler database 33a as shown in FIG. 3. An identification sign (ID) indicating the type of the elastic coupler 20 which has been attached to the probe 1 is input from the control interface unit 19 to the pressurizing-state calculator 33 by an operator. In addition, one or a plurality of identification signs of the elastic coupler 20, and the elasticity property and the speed of sound corresponding to the respective identification signs are input and set in advance in the coupler database 33a.

The pressurizing-state calculator 33 is configured to have an initialization process unit 34, a pressurized-state detector 35, a coupler pressurization evaluation unit 36, a pressure converter 37, a coupler database 33a, and a pressurizing-state image constructing unit 38 as shown in FIG. 4.

The initialization process unit 34 detects that the elastic coupler 20 is in the initial state with no pressure being applied based on the intensity change in the RF signal of the RF signal frame data and obtains an initial thickness of the elastic coupler 20 based on the RF signal when the elastic coupler 20 is in the initial state.

The pressurized-state detector 35 automatically detects that the elastic coupler 20 is in the pressurized state, that is, the state in which the ultrasonic examination is being performed by placing the probe 1 on the body surface of the test body. In addition, it is also applicable that the execution of the ultrasonic examination is input from the control interface unit 19.

The coupler pressurization evaluation unit 36 obtains a thickness detection value in the pressurized state of the elastic coupler 20 and calculates the thickness change with respect to the initial thickness in the initial state. The thickness change in this case corresponds to a total distortion amount (sum of the distortion amounts) of the contact surface of the elastic coupler 20 from the initial state.

The pressure converter 37 reads the thickness change of the elastic coupler 20 calculated by the coupler pressurization evaluation unit 36 and the elasticity property corresponding to the ID of the elastic coupler 20, which was input and set in advance from the control interface unit 19, from the coupler database 33i a and converts the read thickness change and the elasticity property into an absolute pressure applied to the test object 100. In addition, the thickness change and the elasticity property are converted into the absolute pressure by the pressure converter 37 based on the total distortion amount, in the case where the total distortion amount has been obtained by the coupler pressurization evaluation unit 36. Moreover, the coupler pressurization evaluation unit 36 and the pressure converter 37 may be integrally configured.

The pressurizing-state image constructing unit 38 constructs a pressurizing-state image in order to cause the image display 9 to display the absolute pressure output from the pressure converter 37. The pressurizing-state image is at least one of a numerical value of the absolute pressure, a graph of the temporal change, a bar chart, and the like and is converted into color image data by the color scan converter 14. With this configuration, it is possible to display the color image data while aligning or partially overlapping it with the ultrasonic image such as the tomographic image or the elasticity image displayed on the image display 9 by the switch adder 8.

Hereinafter, a detailed description will be made of the pressurizing-state evaluation process by the pressurizing-state evaluation unit 30 of this example with reference to the flow chart shown in FIGS. 3, 4, and 5.

[S1: Starting of Ultrasonic Diagnostic Apparatus]

The ultrasonic diagnostic apparatus is manually started. The test mode is for a test by a B mode tomographic image, for example.

[S2: Coupler Attachment Detection]

The elastic coupler 20 is attached manually to the ultrasonic wave transmitter/receiver surface 1a of the probe 1 as shown in FIG. 2(D). The coupler attachment detector 31 automatically detects the attachment of the elastic coupler 20.

(Example 1 of Coupler Attachment Detection)

Figure 6:
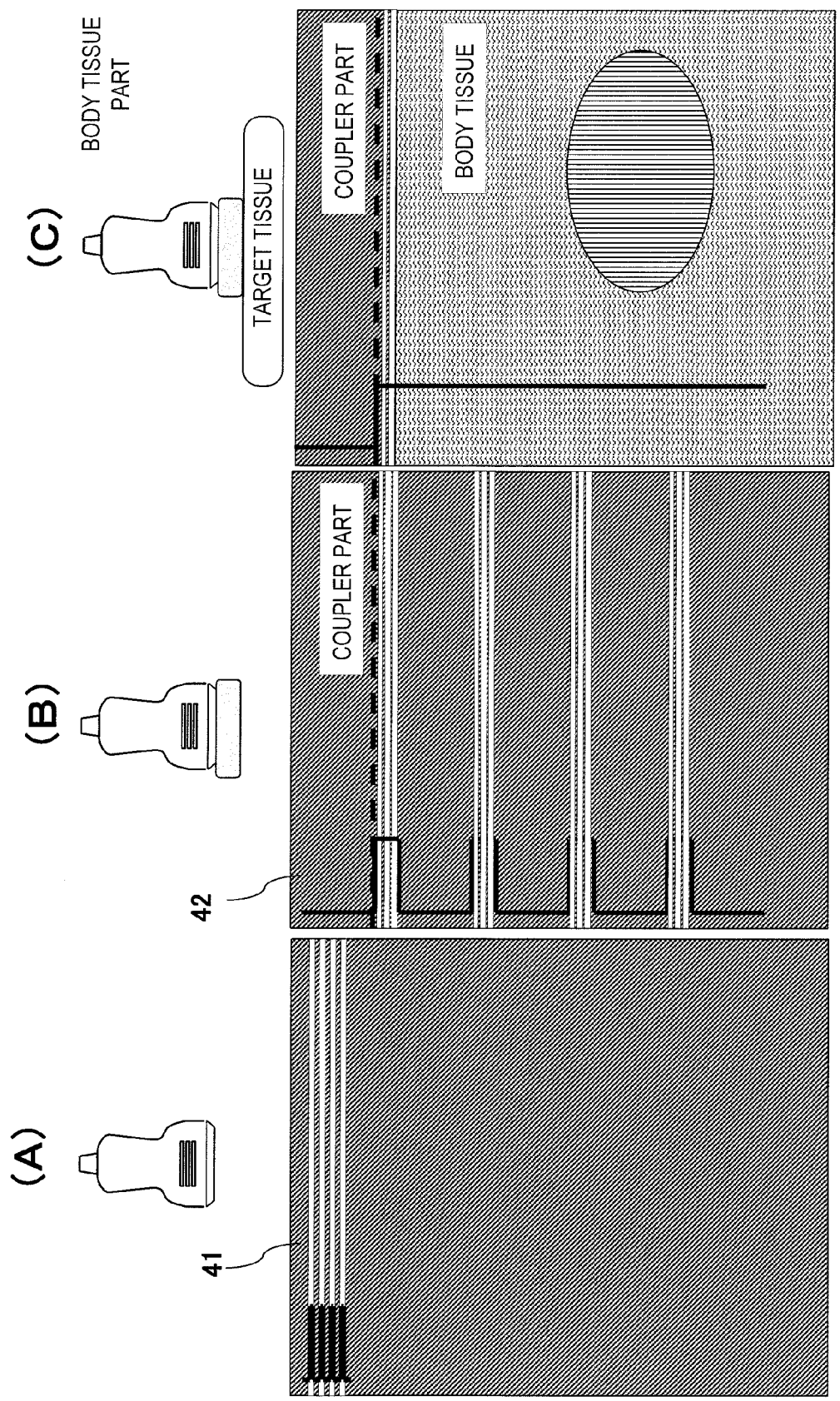
FIG. 6 is a diagram illustrating a principle of detecting an initial state and a pressurized state in Example 1.

A description will be made of the principle of detecting whether or not the elastic coupler 20 has been attached to the ultrasonic wave transmitter/receiver surface 1a with reference to FIG. 6. If the elastic coupler 20 is held in the air and an ultrasonic beam for the B mode test is transmitted in the state where the elastic coupler 20 is not attached to the probe 1, the RF signal including a periodical multiple echo 41 originated from an acoustic lens (with the thickness of about 1 mm) is received in the depth region close to the ultrasonic wave transmitter/receiver surface as the B mode image shown in FIG. 6(A). On the other hand, if the elastic coupler 20 (with the thickness of about 5 to 10 mm, for example) is attached, the multiple echo 41 disappears, and the RF signal including the periodical multiple echo 42 originated from the elastic coupler 20 is received as the B mode image shown in FIG. 6(B). This multiple echo is generated due to a sudden change of the acoustic impedance at the boundary between the exposure surface of the acoustic lens and the air or at the boundary between the exposure surface of the elastic coupler 20 and the air.

Thus, the coupler attachment detector 31 receives the RF signal output from the RF signal frame data selection unit 10, detect a frequency T in which the intensity of the received RF signal exceeds a pre-set threshold value, and determines which one of a frequency Tr corresponding to the thickness of the acoustic lens and a frequency Tc corresponding to the thickness of the elastic coupler 20 the detected frequency is, and detects that the elastic coupler 20 has been attached. Since the frequencies Tr and Tc differ significantly from each other, the determination can be easily made.

Although the description was made of an arbitrary one point in the alignment direction (long axis direction) of the oscillator of the probe 1, in regard to the measurement point ij in the region of the coordinate i (i=0 to n) in the scanning direction of the ultrasonic beam, which is the long axis direction, and the coordinate j (j=0 to m) in the depth direction, an average value $Q^*ij$ ($=\Sigma Qij/(n+1)$) of the intensity Qij of the RF signal (or the illuminance) of the measurement point at the coordinate j with the same depth is obtained. Then, all the coordinates J=j in which $Q^*ij$ is greater than the pre-set threshold value Qthres is obtained, the coordinate frequency T of J is calculated, and the attachment of the elastic coupler 20 is detected depending on the size of the frequency T. For example, if C represent the speed of sound inside the elastic coupler 20, the initial thickness D(0) of the elastic coupler 20 can be calculated by the formula $D(0)=T \cdot C/2$.

In addition, the coupler attachment detector 31 can receive the illuminance data or the signal intensity of the B mode image output from the signal process unit 6 instead of the RF signal output from the RF signal frame data selection unit 10, detect the frequency T in which the illuminance or the signal intensity of the received B mode image exceeds the pre-set threshold value, determine which one of Tr and Tc the detected frequency is, and detect that the elastic coupler 20 has been attached.

(Example 2 of Coupler Attachment Detection)

It is possible to detect that the elastic coupler 20 has been attached by forming layers of scattering bodies for scattering the ultrasonic waves inside the plate-shaped unit of the elastic coupler 20, receiving the RF signal or the illuminance data of the ultrasonic image created based on the RF signal, and detecting the ultrasonic scattering bodies based on the intensity distribution of the received RF signal or the illuminance distribution of the ultrasonic image. As the scattering bodies, it is possible to use a material such as graphite powder or polyethylene powder which has a different acoustic impedance from that of the material of the elastic coupler 20.

It is possible to detect the attachment of the elastic coupler 20 based on whether or not the echo signal of the ultrasonic scattering bodies are included in the RF signal within the time (coupler echo region) of the RF signal corresponding to 0 to 10 mm, in the case where the initial thickness D(0) of the elastic coupler 20 is from 5 to 10 mm, for example.

According to Example 2, it is possible to detect the attachment of the elastic coupler 20 with easier signal process than that in Example 1 of the coupler attachment detection.

Although the example in which one or a plurality of layers of the scattering bodies is formed was described in Example 2, the scattering bodies may be dispersed and mixed entirely in the elastic coupler 20. With such a configuration, it is possible to increase the intensity of the RF signal in the coupler echo region and thereby to enhance the detection accuracy.

(Example 3 of Coupler Attachment Detection)

Figure 7:
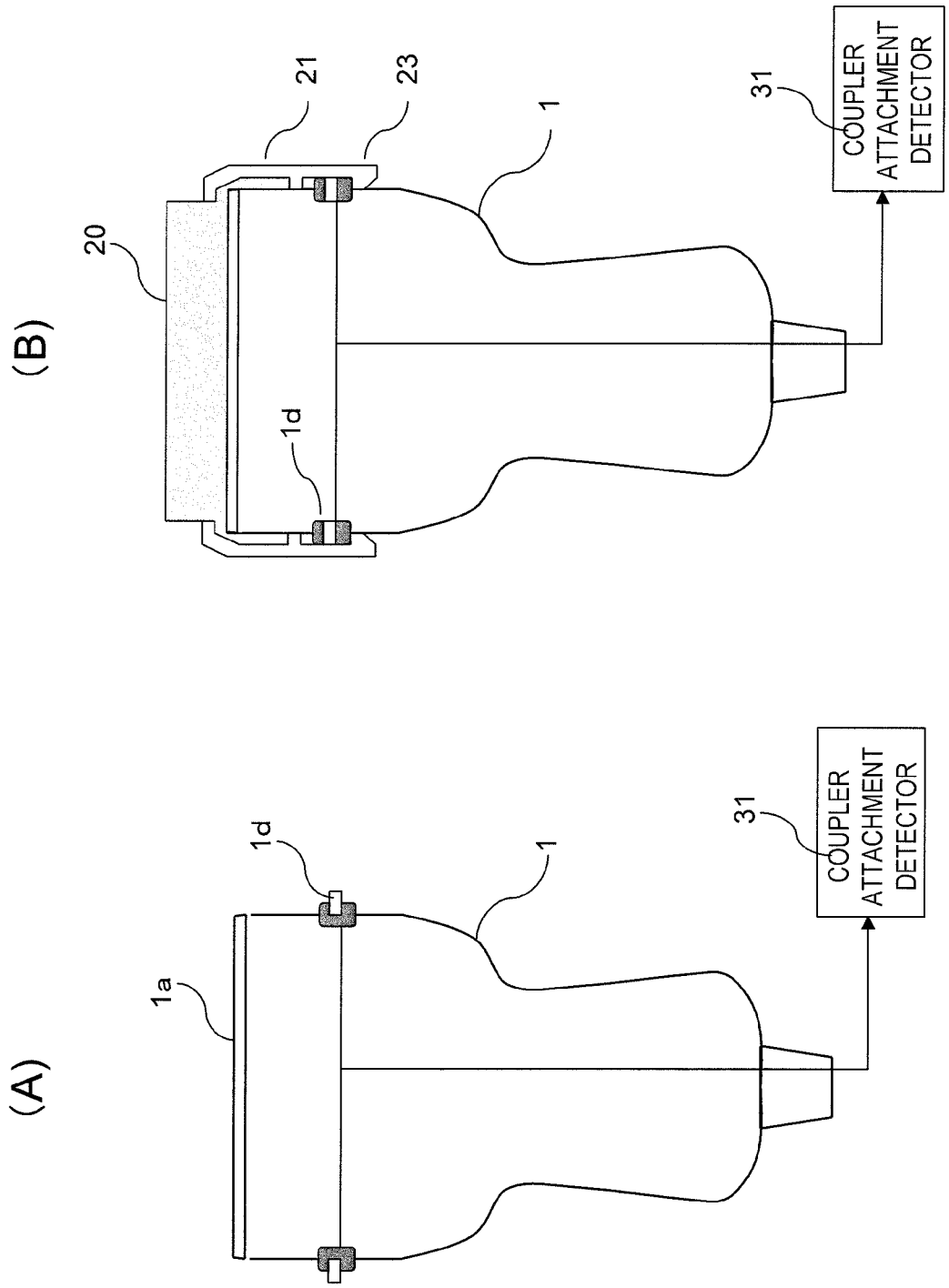
FIG. 7 is a configuration diagram of another example for detecting the attachment of the elastic coupler.

Although the attachment of the elastic coupler 20 is detected based on the RF signal in Examples 1 and 2 of the coupler attachment detection, the invention is not limited thereto, and it is possible that an attachment sensor $1d$ constituted by a switch or the like which moves toward and retreats from the locking portion $1b$ of the probe 1 is provided, the locking claw 23 of the attachment tool 21 is detected by the attachment sensor $1d$ when the elastic coupler 20 is attached as shown in FIG. 7(B), and the coupler attachment detector 31 is prompted to input the attachment detection signal. With such a configuration, the coupler attachment detector 31 can easily detect that the elastic coupler 20 has been attached.

[S3: Identification of Elastic Coupler]

Generally, the pressurizing force is different in some cases depending on the testing item of the ultrasonic wave. In order to handle this, it is preferable to prepare plural types of elastic couplers 20 with different thicknesses and elasticity properties and replace and use the elastic coupler 20 in accordance with the testing item since it is possible to accurately detect the absolute pressure.

However, the principle of detecting the absolute pressure according to the invention is based on the fact that the thickness of the elastic coupler 20 changes in a correlation with an applied pressurizing force (absolute pressure) and that the correlation depends on the elasticity property of the elastic coupler 20. Thus, it is necessary to measure and set in advance the elasticity property of the elastic coupler 20 including at least elastic modulus and the like in order to obtain the absolute pressure.

Accordingly, in this example, the type of the elastic coupler is identified by inputting the ID of the elastic coupler 20 attached to the probe 1 from the control interface unit 19 to the pressurizing-state calculator 33 by the user.

[S4: Starting of Pressurizing-State Calculator]

The pressurizing-state calculator 33 is started when the attachment of the elastic coupler 20 is detected by the coupler attachment detector 31. Alternatively, it is possible to configure the pressurizing-state calculator 33 to be started when the operator inputs the fact that the elastic coupler 20 has been attached from the control interface unit 19.

[S5: Creation of Initial State]

Although the initial thickness D(0) of the elastic coupler 20 can be measured in advance, it is considered that the initial thickness D(0) changes due to the temporal change such as evaporation of the liquid component in the gel-like material which is a material of the elastic coupler 20. For this reason, it is preferable to automatically measure the initial thickness D(0) in the initial state every time the ultrasonic examination is performed in order to accurately detect the absolute pressure.

In this example, the initial state in which the operator grips the probe 1 and holds it in the air is automatically recognized by the initialization process unit 34 based on the multiple echo, as described above, in order to automatically measure the initial thickness D(0) in the initial state with no pressure being applied, in which the exposure surface of the elastic coupler 20 is held in the air.

In addition, it is possible to manually order the initialization process unit 34 from the control interface unit to perform the automatic measurement of the initial thickness D(0) in the state where the operator grips the probe 1 and holds it in the air instead of the automatic recognition of the initial state.

[S6: Initialization Process]

The initialization process unit 34 automatically recognizes the initial state where the operator grips the probe 1 and holds it in the air and automatically measures the initial thickness D(0) in the initial state of the elastic coupler 20. Hereinafter, a description will be made of specific examples.

(Example of Automatic Recognition of Initial State)

In regard to the initial state where the operator grips the probe 1 and holds it in the air, it is possible to automatically recognize that the elastic coupler 20 is in the initial state by receiving the RF signal output from the RF signal frame data selection unit 10, detecting the frequency T in which the intensity of the received RF signal exceeds the pre-set threshold value, and detecting that the detected frequency is the frequency Tc corresponding to the thickness of the elastic coupler 20 as described in Example 1 of the coupler attachment detection in S2.

(Example of Obtaining Initial Thickness D(0))

Next, a description will be made of the example of obtaining the initial thickness D(0) of the elastic coupler in the initial state of the elastic coupler 20. The initialization process unit 34 transmits the ultrasonic waves in the initial state in which no pressure is being applied, receives the current RF signal from the RF signal frame data selection unit 10, recognizes that the elastic coupler 20 is in the initial state, and then obtains the position of the exposure surface of the elastic coupler 20.

That is, time $ti(0)$ is obtained during which the intensity of the RF signal changes significantly after the ultrasonic waves are transmitted from the transmitting circuit 2 to the probe 1. Here, i represents a coordinate position in the scanning direction of the ultrasonic beam of the elastic coupler 20 as described above.

In addition, $ti(0)$ is a time for the round travel of the ultrasonic waves reflected from the exposure surface of the elastic coupler 20. Accordingly, it is possible to obtain a thickness distribution initial value $Di(0)$, which is a one-dimensional distribution in the scanning direction, by multiplying $ti(0)$ by the speed of sound C and then dividing the obtained value by 2. In addition, it is also possible to obtain $Di(0)$ by obtaining the frequency (frequency of not less than the threshold value) T in which the intensity of the RF signal changes significantly, multiplying T by the speed of sound, and dividing the obtained value by 2. Moreover, it is possible to similarly obtain the thickness distribution initial value $Di(0)$ of the elastic coupler 20 by obtaining $ti(0)$ during which the illuminance of the B mode tomographic image created based on the RF signal changes significantly or obtaining the frequency (frequency of not less than the threshold value) T.

In addition, in regard to the initial thickness distribution $Di(0)$ of the elastic coupler 20, it is possible to obtain a two-dimensional distribution of the initial thickness distribution to which the distribution in the direction perpendicular to the scanning direction is added.

[S7: Measurement of Coupler Deformation (Distortion)]

The process in S7 is a process by the pressurized-state detector 35 and the coupler pressurization evaluation unit 36 in FIG. 4. First, the pressurized-state detector 35 detects that the elastic coupler 20 is in the pressurized state based on the fact that the multiple echo, in which the intensity of the RF signal exceeds the pre-set threshold value and periodically changes, due to the elastic coupler 20 has disappeared, as described in Example 1 of the coupler attachment detection in S2

The coupler pressurization evaluation unit 36 detects the boundary between the elastic coupler 20 and the test object 100 based on the RF signal at an arbitrary timing t during the pressurized state of the elastic coupler 20 and obtains the thickness distribution Di(t) in the scanning direction in the pressurized state of the elastic coupler 20. That is, the thickness distribution Di(t) in the scanning direction is obtained based on the speed of sound C and the time ti(t) from the point in time when the operator places the probe 1 on the test object 100 via the elastic coupler 20, applies the pressure, and transmits the ultrasonic waves in the pressurized state to the point in time when the intensity of the RF signal Qi(t) changes significantly.

Subsequently, a thickness change distribution $\Delta Di(t)$ is obtained by the following formula (1) and obtains a total distortion amount distribution Si(t) in the scanning direction perpendicular to the ultrasonic beam (hereinafter, simply referred to as a scanning direction) for the total distortion amount S in the depth direction by the following formula (2).

$$\Delta Di(t)=Di(0)-Di(t) \quad (1)$$

$$Si(t)=\Delta Di(t)/Di(0) \quad (2)$$

[S8: Conversion Process of Absolute Pressure]

The pressure converter 37 uses the elasticity property (for example, the elastic modulus E such as Young's modulus) of the elastic coupler 20 which has been input and set from the control interface unit 19 and stored in the pressure converter 37 based on the total distortion amount distribution Si(t) obtained in Example 1 of the coupler pressurization evaluation unit 36, and converts an absolute pressure distribution Pi(t) applied to the body tissue of the test object 100 by the following formula (3).

$$Pi(t)=Si(t)\times E \quad (3)$$

The current absolute pressure distribution Pi(t) obtained by the conversion is output to the elasticity calculator 12 in FIG. 1. With this operation, the elastic calculator 12 obtains the elastic modulus (for example, Young's modulus) Eij(t) at the respective measurement points i and j by the following formula (4) based on distortion $\epsilon ij(t)$ obtained for the respective measurement points i and j of the body tissue by the known calculation process as described above, and outputs the elastic modulus to the elasticity data process unit 13.

$$Eij(t)=Pi(t)/\epsilon ij(t) \quad (4)$$

[S9: Display Process of Pressurizing State]

The pressurizing-state image constructing unit 38 creates an image of the absolute pressure distribution Pi(t) obtained by the conversion process of the absolute pressure in S8, prompts the image display 9 to display the created image, and thereby makes it possible for the operator to immediately determine whether or not the pressurizing state is appropriate for the test item in the same screen while executing the ultrasonic examination.

That is, the pressurizing-state image constructing unit 38 constructs at least one image from among the numerical value display, the graph display of the temporal change, the bar chart display, and the like from the absolute pressure distribution Pi(t) and display the constructed image while aligning or partially overlapping it with the ultrasonic image displayed on the image display 9.

Figure 8:
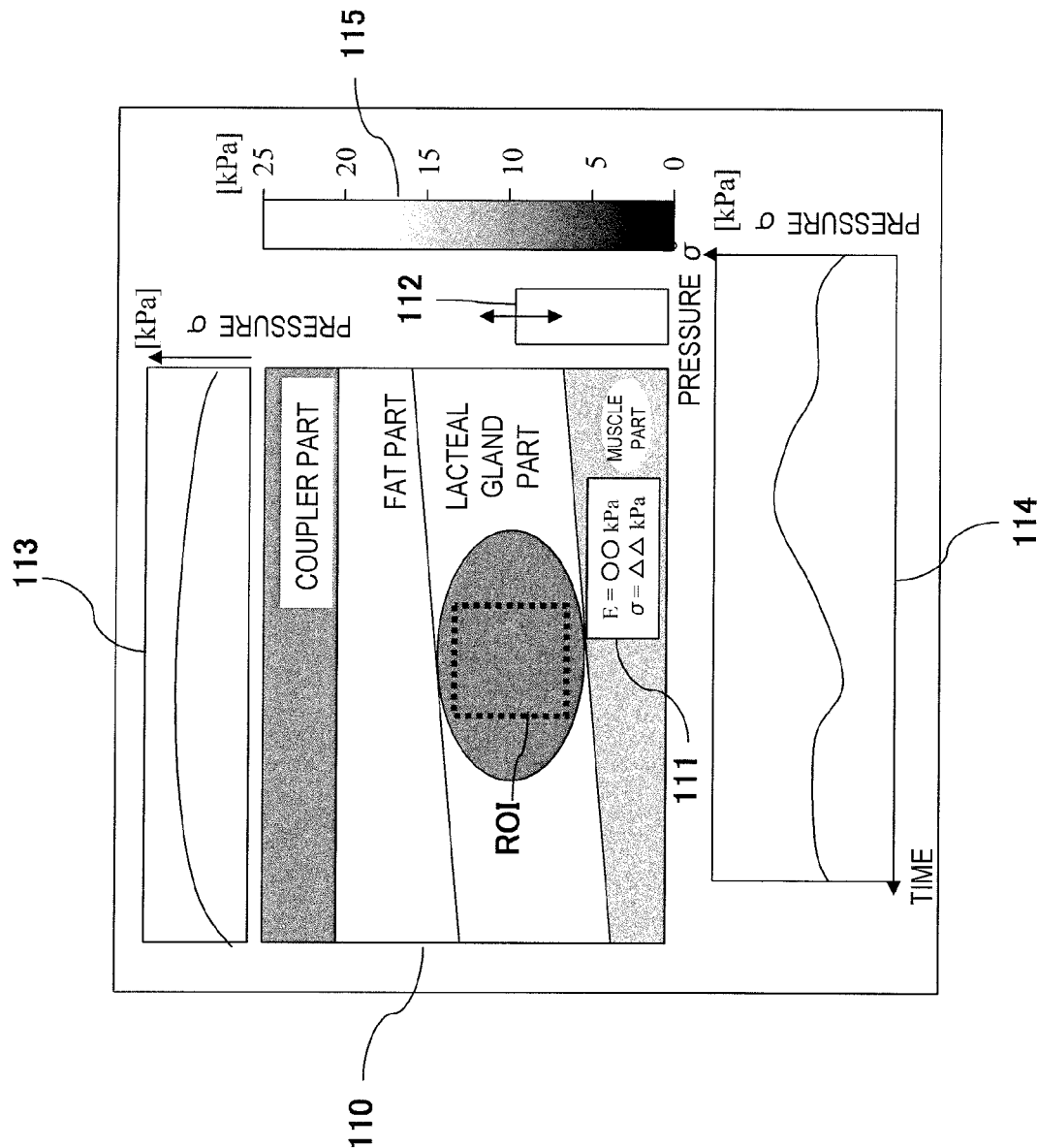
FIG. 8 is a diagram illustrating an example of a pressurizing-state image displayed in Example 1.

FIG. 8 shows an example in which the pressurizing-state image is overlapped or aligned with the elasticity image. In the drawing, the elasticity image 110 is displayed in the center of the screen, and the elastic modulus E (kPa) and the absolute pressure σ (kPa) are displayed as numerical values in the display window 111 near the rectangular region of interest (ROI). In addition, a bar chart 112 is displayed in which the absolute pressure σ at present is an average value of the absolute pressure distribution Pi.

Moreover, a graph 113 of the absolute pressure distribution Pi in the scanning direction is displayed in the upper part of the screen, and a graph 114 of the temporal change in the average value of the absolute pressure distribution Pi is displayed in the lower part of the screen. Furthermore, a color bar 115 of the elastic modulus E is displayed at the right edge of the screen.

Accordingly, the operator can perform diagnosis while evaluating the elasticity of the body tissue of the ROI under an appropriate absolute pressure by observing the image in FIG. 8. Particularly, it is possible to immediately determine whether or not the pressurizing force is appropriate by checking the bar chart 112 of the average value or the like of the absolute pressure distribution Pi.

Figure 9:
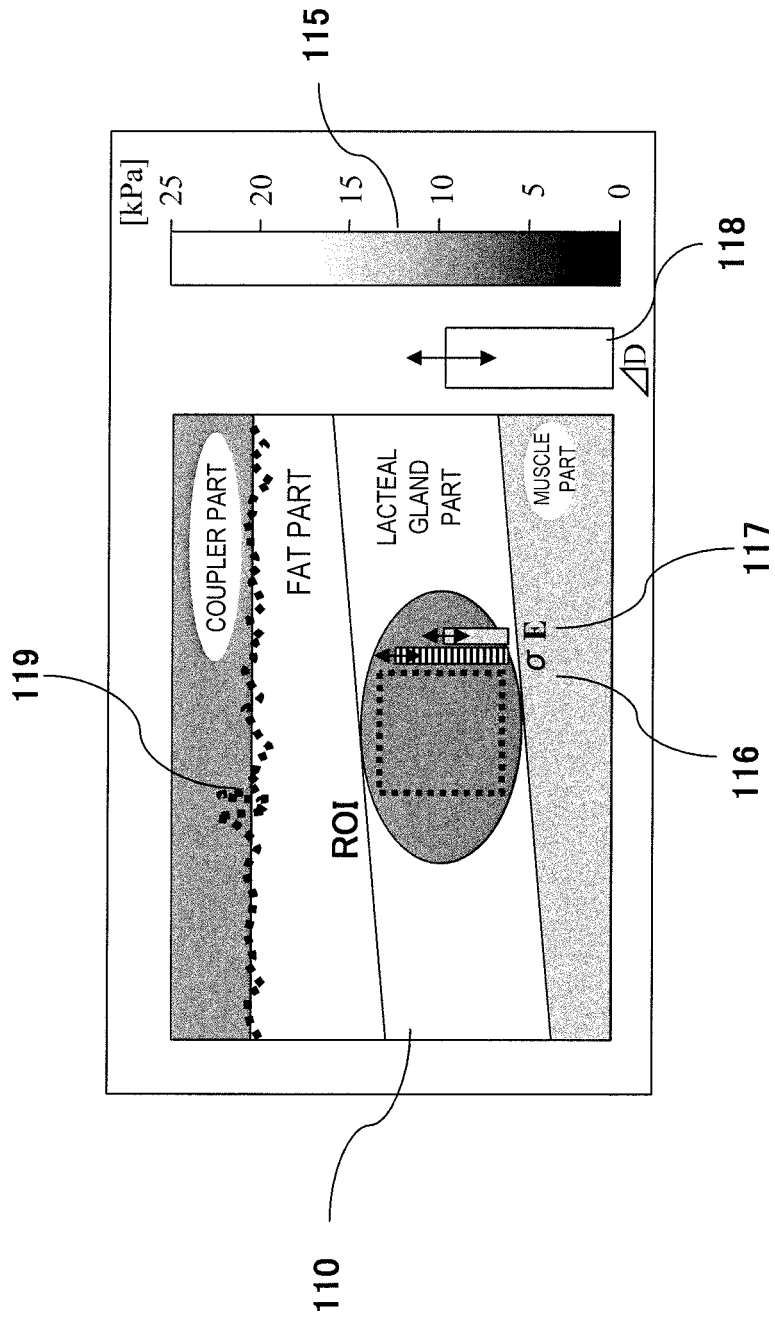
FIG. 9 is a diagram illustrating another example of a pressurizing-state image displayed in Example 1.

FIG. 9 shows another example in which the pressurizing-state image is displayed while being overlapped or aligned with the elastic image. In the same drawing, the elastic image 110 is displayed in the center of the screen, and the elastic modulus (kPa) and the absolute pressure σ (kPa) are displayed in the bar charts 116 and 117 near the rectangular region of interest (ROI). In addition, the bar chart 118 representing the average value in the scanning direction of the thickness change $\Delta Di(t)$ of the elastic coupler from the initial state and the like is displayed. Moreover, the boundary between the elastic coupler and the test body is displayed by a plurality of dots 119 in the upper part of the screen.

It is possible to easily identify whether or not the pressurizing state is appropriate based on the evaluation of the pressurizing-state evaluation unit, for example, by changing the displaying color of the boundary line representing the ROI or by turning on and off the display of the boundary.

Figure 5:
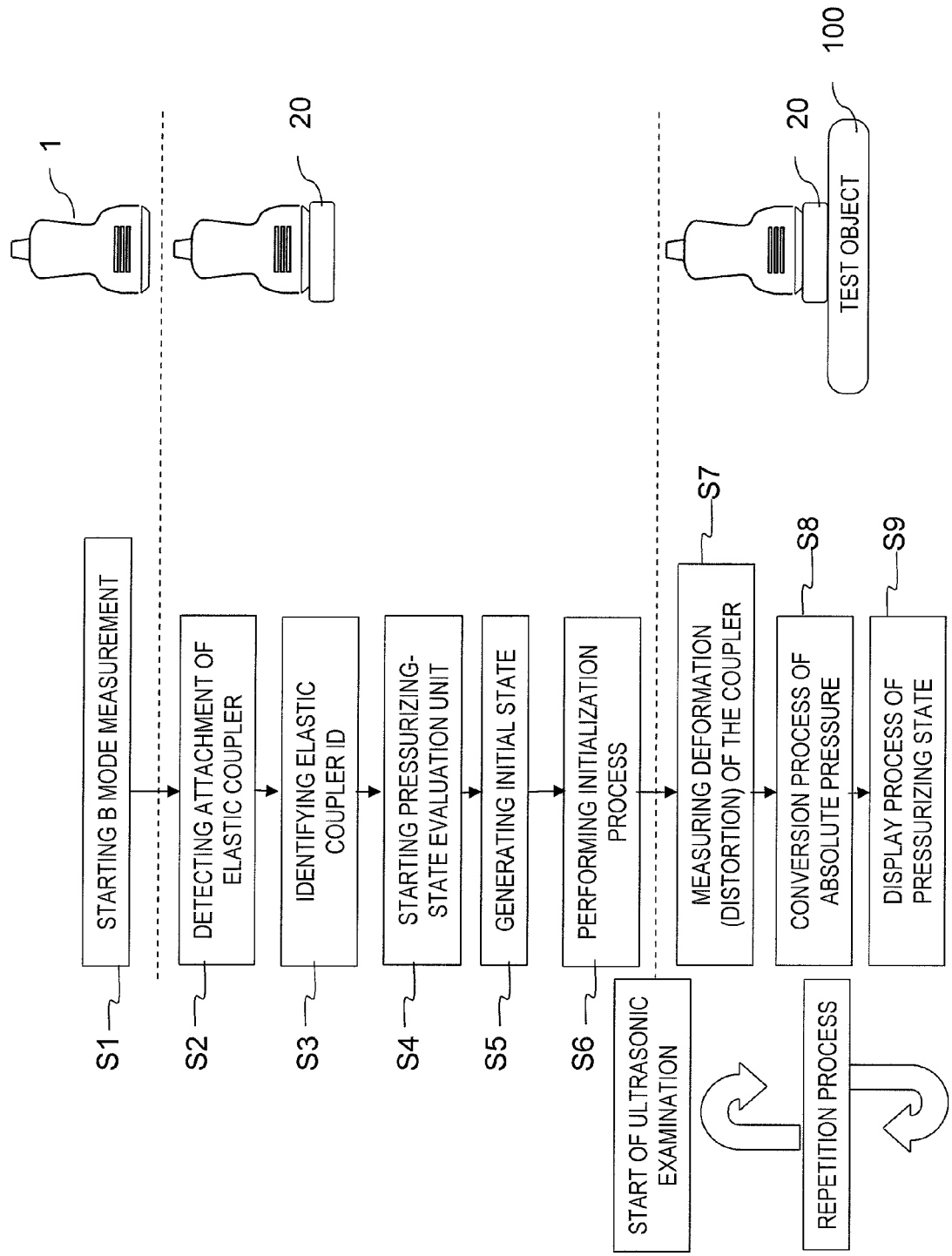
FIG. 5 is a flow chart illustrating process steps of a characteristic unit of Example 1.

As described above, according to this example, it is possible to automatically perform a series of processes of the attachment detection of the elastic coupler 20, the initialization process, the calculation of the absolute pressure, and the diagnosis measurement as shown in FIG. 5.

As a result, it is possible to simplify the operation relating to the detection of the absolute pressure applied to the test body by the probe and thereby to enhance usability.

In addition, since the absolute pressure can be detected in real time, it is possible to evaluate whether or not the pressurizing state is appropriate for the respecting testing methods by monitoring the pressurizing state suitable for various testing methods and thereby to support the test in an appropriate pressurizing state regardless of the extent of the experience of the operator. As a result, it is possible to secure objectivity and prevent erroneous diagnosis.

In addition, the thickness or the like becomes thinner over time due to the evaporation of the liquid component and the property is changed since the material of the elastic coupler is a gel-like material. Therefore, in addition to Example 1, it is preferable to measure the initial thickness of the elastic coupler every time the initialization process of the coupler is performed, compare the initial thickness with the reference value, and give a warning that the expiration date for use has passed when there is a difference which is not less than the set range.

In addition, it is possible to send a feedback regarding the thickness of the elastic coupler obtained in the initialization process to the transmitting circuit 2 and the receiving circuit 3, automatically adjust the focus depth, and thereby to maintain the resolution of the ultrasonic image, so as to match the attachment of the elastic coupler or even if the thickness of the elastic coupler is changed. Moreover, it is preferable to reset the depth of the ROI to be deeper so as to match the attachment of the elastic coupler.

In addition, by cutting the displayed image of the elastic coupler in accordance with the thickness of the elastic coupler obtained in the initialization process or the like, it is possible to display the image of the deeper body tissue by the amount corresponding to the cut image.

EXAMPLE 2

Figure 10:
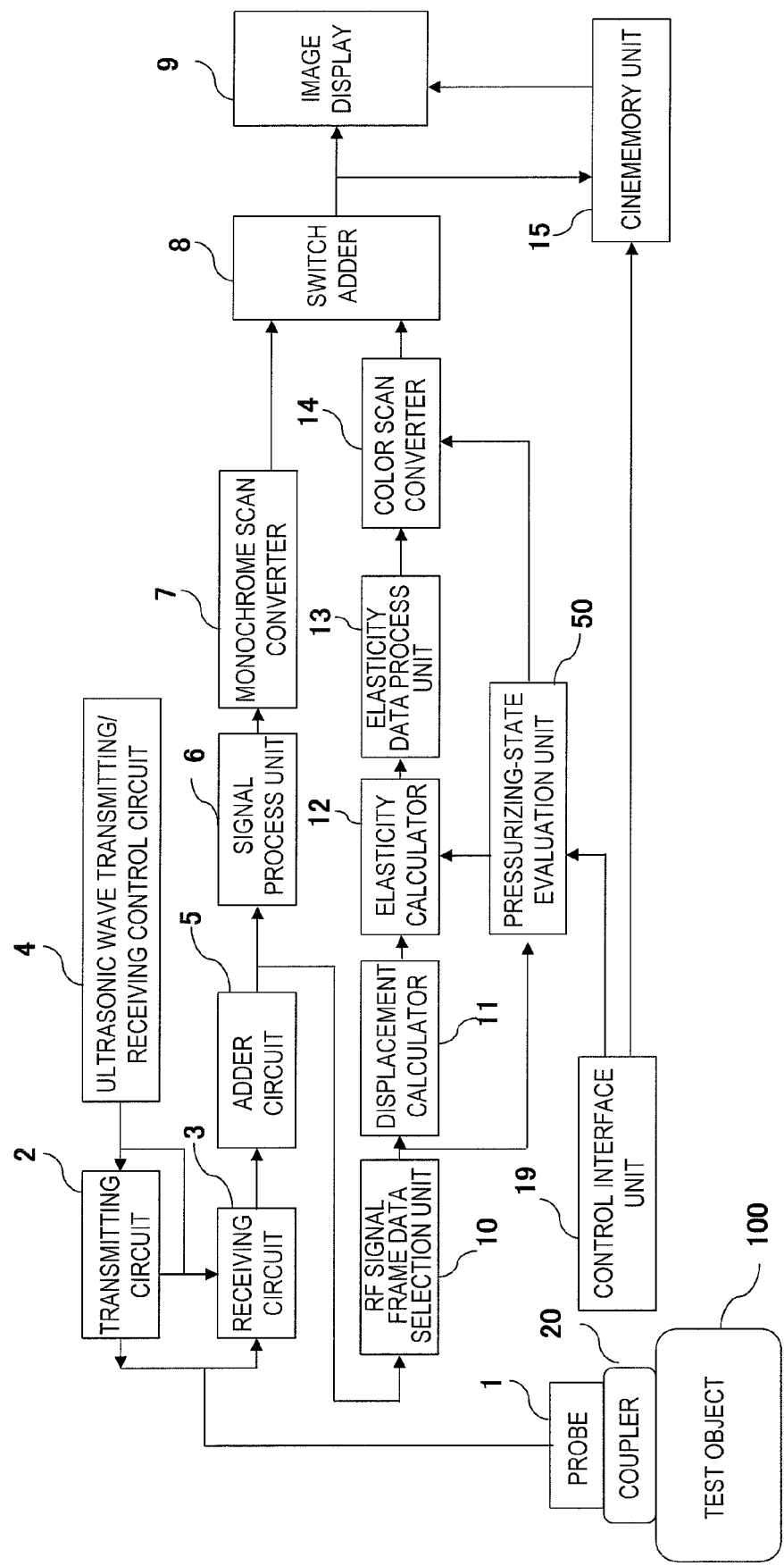
FIG. 10 is a block configuration diagram of an ultrasonic diagnostic apparatus of Example 2 of the invention.

FIG. 10 is a functional block configuration diagram of the ultrasonic diagnostic apparatus of another example of the invention. As shown in the same drawing, the difference between this example and Example 1 in FIG. 1 is the configuration of the pressurizing-state evaluation unit 50, and other configurations are the same as those in Example 1. Accordingly, the same reference numerals are added, and the description will be omitted. In addition, the detailed functional block configuration diagrams of the pressurizing-state evaluation unit 50 of this example will be shown in FIGS. 11 and 12.

Figure 11:
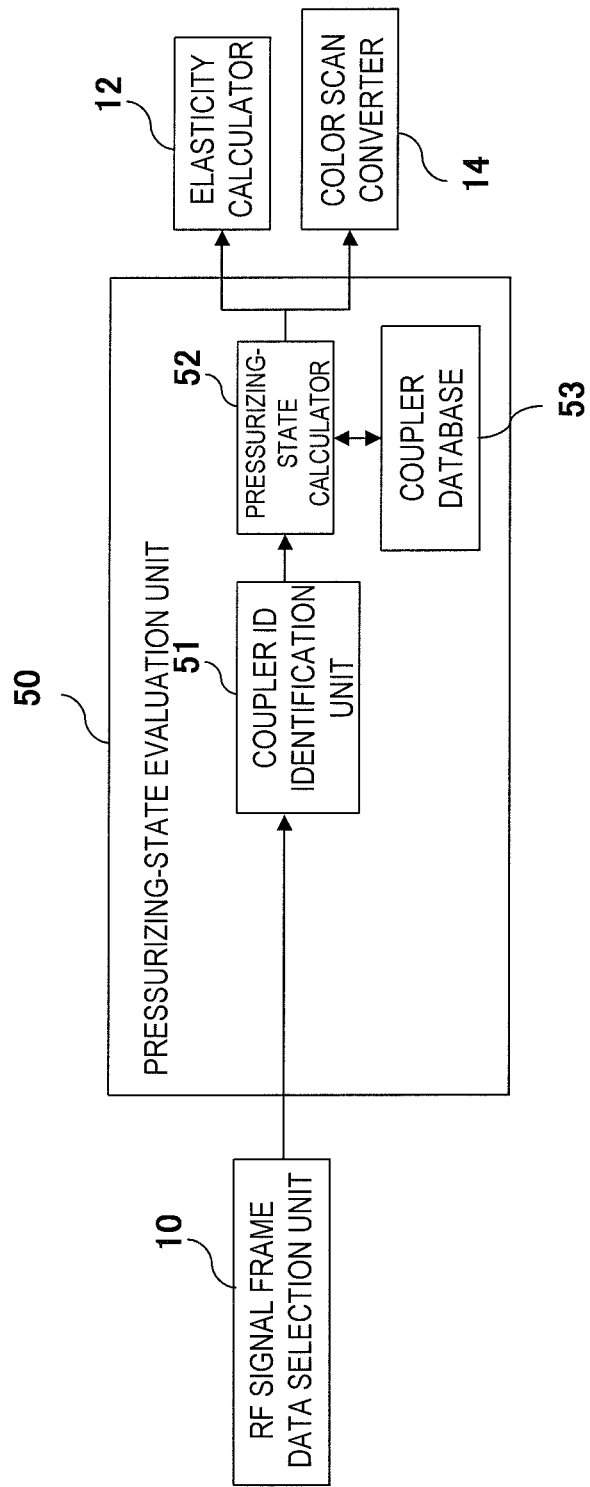
FIG. 11 is a block configuration diagram illustrating a detailed configuration of a pressurizing-state evaluation unit of Example 2.
Figure 12:
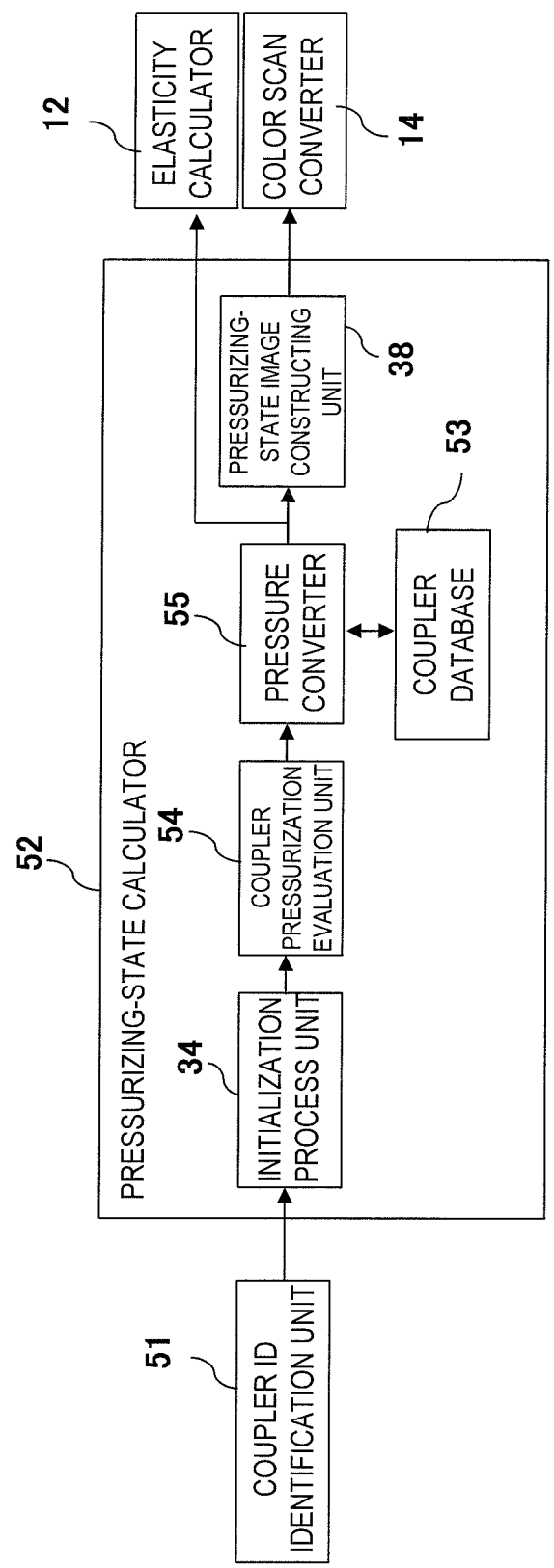
FIG. 12 is a block configuration diagram illustrating a detailed configuration of a pressurizing-state calculator of Example 2.

As shown in FIGS. 11 and 12, the pressurizing-state evaluation unit 50 of this example is different from that in Example 1 in that the pressurizing-state evaluation unit 50 of this example does not include the coupler attachment detector 31 and the pressurized-state detector 35.

The pressurizing-state evaluation unit 50 of this example is configured to have a coupler ID identification unit 51, a pressurized-state calculator 52, and a coupler database 53 as shown in FIG. 11.

In addition, although the elastic coupler applied to this example has the same shape as those shown in FIGS. 2(A) and 2(B), an elastic coupler 20 is used, to which a unique identification code (ID) is given, for example, by making the depth of the layer of the ultrasonic scattering bodies or the number of the layers to be different depending on the type of the elastic coupler 20. Moreover, it is also applicable to code the elastic coupler 20 with ID by dispersing and mixing the scattering bodies entirely in the elastic coupler 20, and causing the disperse density of the scattering bodies to be different. Furthermore, it is also possible to give an ID code in accordance with the type of the elastic coupler 20 by forming the code regions, in which the scattering bodies coded in the scanning direction are dispersed, in the regions in both the edges of the elastic coupler 20 in the scanning direction, which are apart from the region of interest (ROI).

With such a configuration, the coupler ID identification unit 51 can automatically recognize the ID of the elastic coupler 20 and identify the type of the elastic coupler 20 by detecting the depth distribution pattern of the RF signal or the like within the coupler echo region. Moreover, it is possible to give an ID code in accordance with the type of the elastic coupler 20 by forming the code regions, in which the scattering bodies coded in the scanning direction are dispersed, in the regions in both the edges of the elastic coupler 20 in the scanning direction, which are apart from the region of interest (ROI). It is possible to integrally implement the above-mentioned coupler attachment detection by using such the identification code of the scattering bodies, which represents the type of the elastic coupler.

The coupler ID identification unit 51 receives the RF signal frame data in the ordinary test from the RF signal frame data selection unit 10, detects the ID code by the depth distribution of the RF signal or the like within the coupler echo region or the ID code of the sign region, and automatically recognizes the type of the elastic coupler 20. The ID code of the elastic coupler 20, which has been identified by the coupler ID identification unit 51, is output to the pressurizing-state calculator 52.

The pressurizing-state calculator 52 is configured to have the initialization process unit 34, the coupler pressurization evaluation unit 54, the pressure converter 55, and the pressurizing-state image constructing unit 38 as shown in FIG. 12. The initialization process unit 34 and the pressurizing-state image constructing unit 38 are configured to be the same as those in Example 1.

Figure 13:
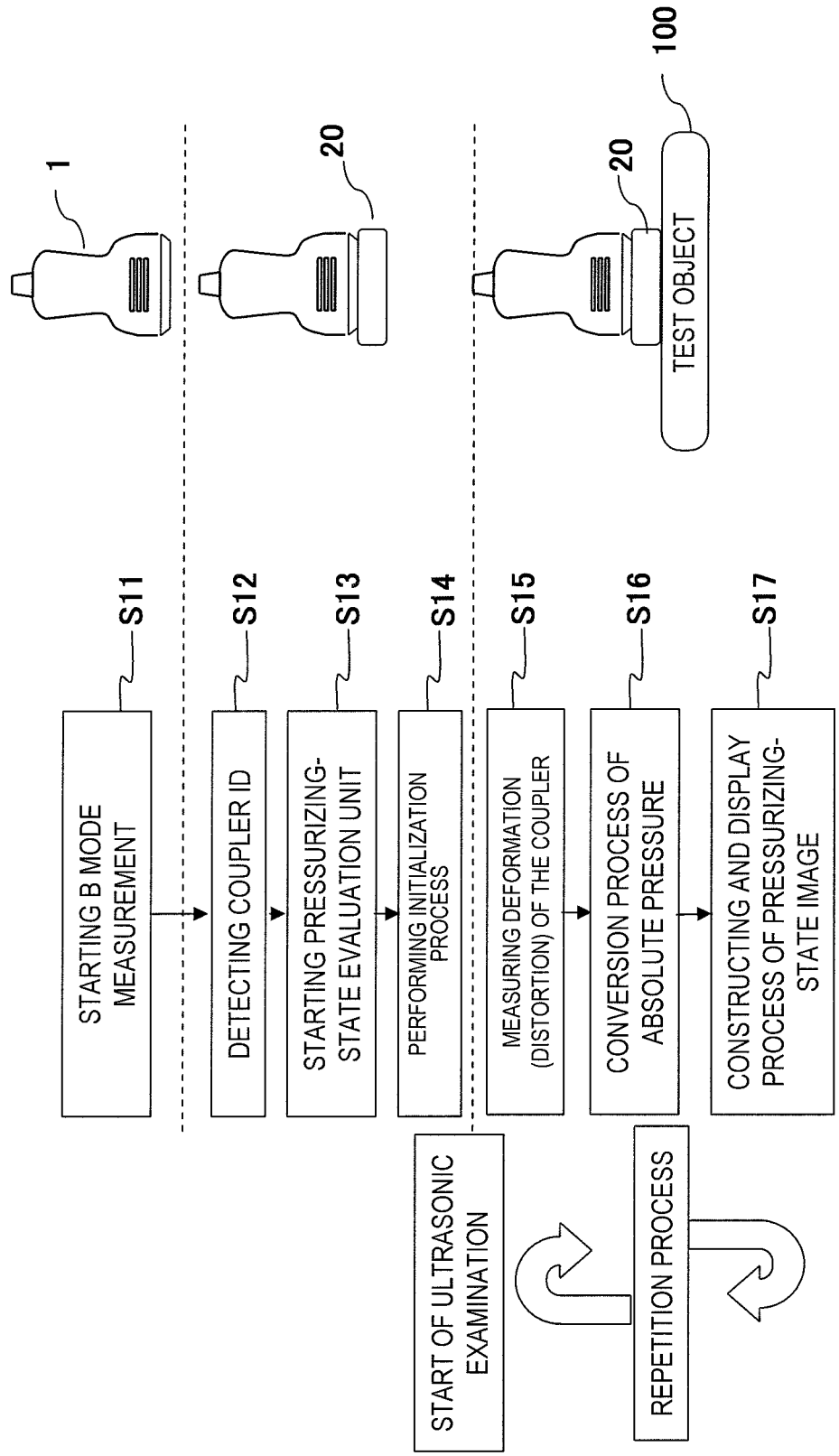
FIG. 13 is a flow chart illustrating process steps of a characteristic unit of Example 2.

Hereinafter, a detailed description will be made of the pressurizing-state evaluation process by the pressurizing-state evaluation unit 50 of this example with reference to the flow chart shown in FIG. 13.

[S11: Starting of Ultrasonic Diagnostic Apparatus]

The ultrasonic diagnostic apparatus is manually started. The test mode is for a test by a B mode tomographic image, for example.

[S12: Coupler ID Identification]

Since the pressurizing force is generally different in accordance with the testing item of the ultrasonic waves, it is preferable to replace and use a plurality of types of elastic couplers 20 with different thicknesses and elasticity properties in accordance with the testing item. In this example, it is possible to identify the type by forming the ID code region in the elastic coupler 20.

The coupler ID identification unit 51 of this example receives the RF signal frame data in the ordinary test from the RF signal frame data selection unit 10, detects the ID code by the depth distribution of the RF signal or the like within the coupler echo region or the ID code in the code region, automatically recognizes the type of the elastic coupler 20, and outputs the ID code of the elastic coupler 20 to the pressurizing-state calculator 52.

[S13: Starting of Pressurizing-State Calculator]

The pressurizing-state calculator 52 is started when the ID of the elastic coupler 20, which has been automatically identified by the coupler ID identification unit 51, is input.

[S14: Execution of Initialization Process]

The initialization process unit 34 automatically recognizes the initial state, in which the operator grips the probe 1 and holds it in the air, in the same manner as in Example 1, and automatically measures the initial thickness distribution Di(0) in the initial state of the elastic coupler 20.

[S15: Coupler Deformation (Distortion) Measurement]

(Example 1 of Coupler Pressurization Evaluation)

The coupler pressurization evaluation unit 54 detects the boundary between the elastic coupler 20 and the test object 100 based on the RF signal at an arbitrary timing t in the pressurized state of the elastic coupler 20 and obtains the thickness distribution Di(t) in the scanning direction in the pressurized state of the elastic coupler 20 similarly to the coupler pressurization evaluation unit 36 in Example 1. That is, the thickness distribution Di(t) in the scanning direction is obtained based on the speed of sound C and the time ti(t) from the point in time when the operator places the probe 1 on the test object 100 via the elastic coupler 20, applies a pressure, and transmits the ultrasonic waves in the pressurized state to the point in time when the intensity of the RF signal Qi(t) changes significantly.

Then, the thickness change distribution ΔDi(t) is obtained by the above formula (1) and the total distortion amount distribution Si(t) in the scanning direction perpendicular to the ultrasonic beam is obtained for the total distortion amount S in the depth direction by the above formula (2).

(Example 2 of Coupler Pressurization Evaluation)

The coupler pressurization evaluation unit 54 can obtain the total distortion amount Sij(t) by obtaining the displacement of the measurement point within the elastic coupler at the respective measurement points in time based on the RF signal frame data Qij(0) of the coupler echo region in the initial state, which is output from the RF signal frame data selection unit 10, and the RF signal frame data Qij(t) which is output from the RF signal frame data selection unit 10 at an arbitrary timing t in the pressurized state. Here, i is a coordinate in the scanning direction of the elastic coupler 20, and j is a coordinate of the thickness direction (depth direction) of the elastic coupler 20 as described above.

Figure 14:
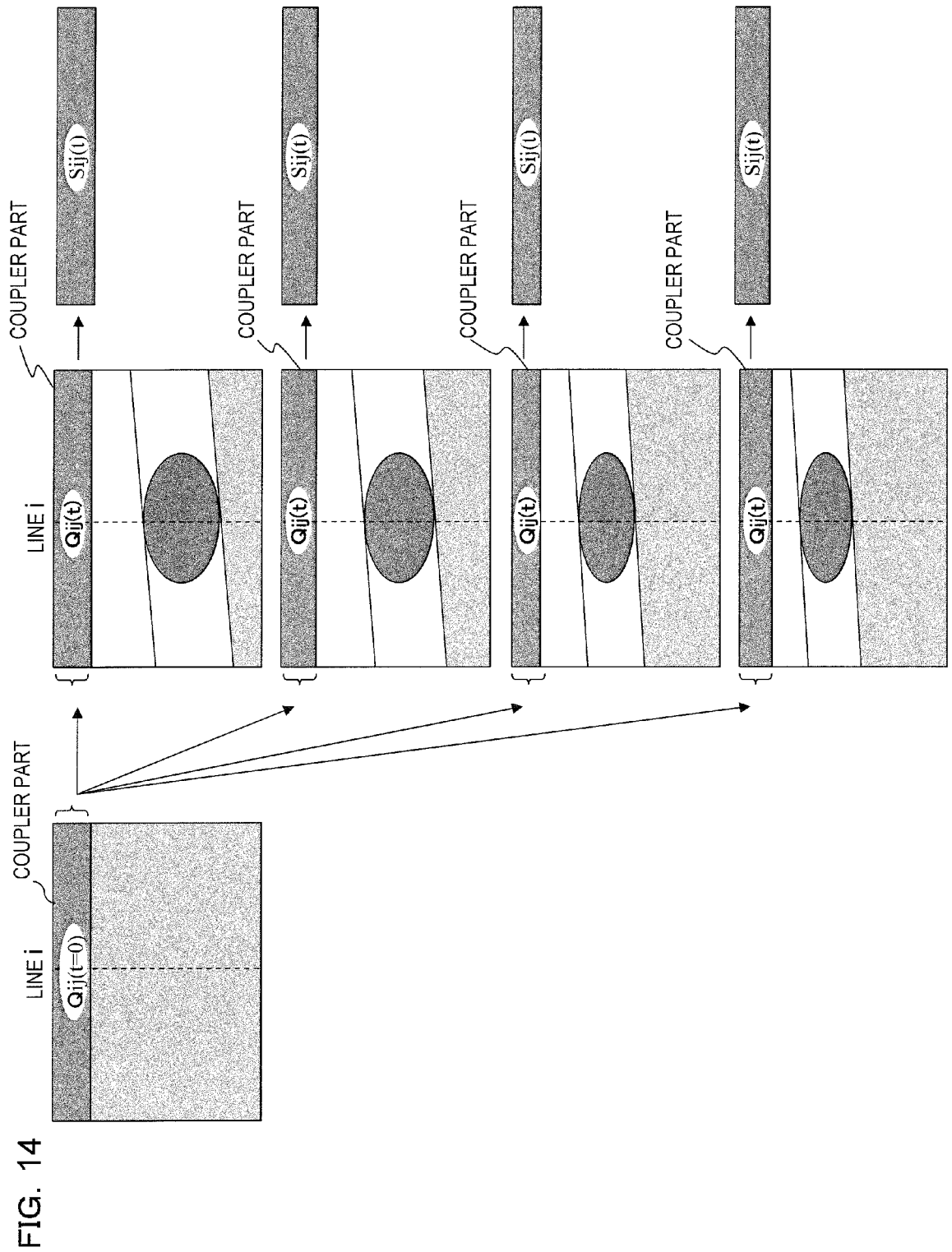
FIG. 14 is a diagram illustrating an example of a process by a coupler pressurization evaluation unit of Example 2.

That is, the RF signal frame data receives the RF signal Qij(t) of the coupler echo region, which changes in real time in the pressurized state, obtains the displacement of the respective measurement points i and j by a know displacement calculation method based on Qij(0) in the initial state and Qij(t) at an arbitrary timing t, and generates displacement frame data as shown in FIG. 14. Then, the displacement frame data is subjected to space derivative to obtain distortion frame data including the total distortion amount Sij(t) of the respective measurement points i and j.

Then, an average value Si*(t) of the total distortion amount Sij(t) is obtained over the depth j of the coupler echo region for every coordinate i in the same scanning direction based on the total distortion amount Sij(t) of the distortion frame data, and evaluated as the total distortion amount Sij(t) at the coordinate position i in the ultrasonic wave scanning direction. Then the absolute pressure Pi(t) is obtained by the pressure converter 55 using the evaluated total distortion amount Sij(t).

According to this example, it is possible to perform both the distortion calculation of the body tissue by the elasticity calculator 12 in FIG. 1 and the process for obtaining the absolute pressure Pi(t) at the same time.

In the case of this example, since it is possible to increase the intensity of the RF signal by dispersing and mixing the ultrasonic scattering bodies in the elastic coupler 20, the accuracy in calculating the thickness or the distortion is enhanced.

(Example 3 of Coupler Pressurization Evaluation)

Figure 15:
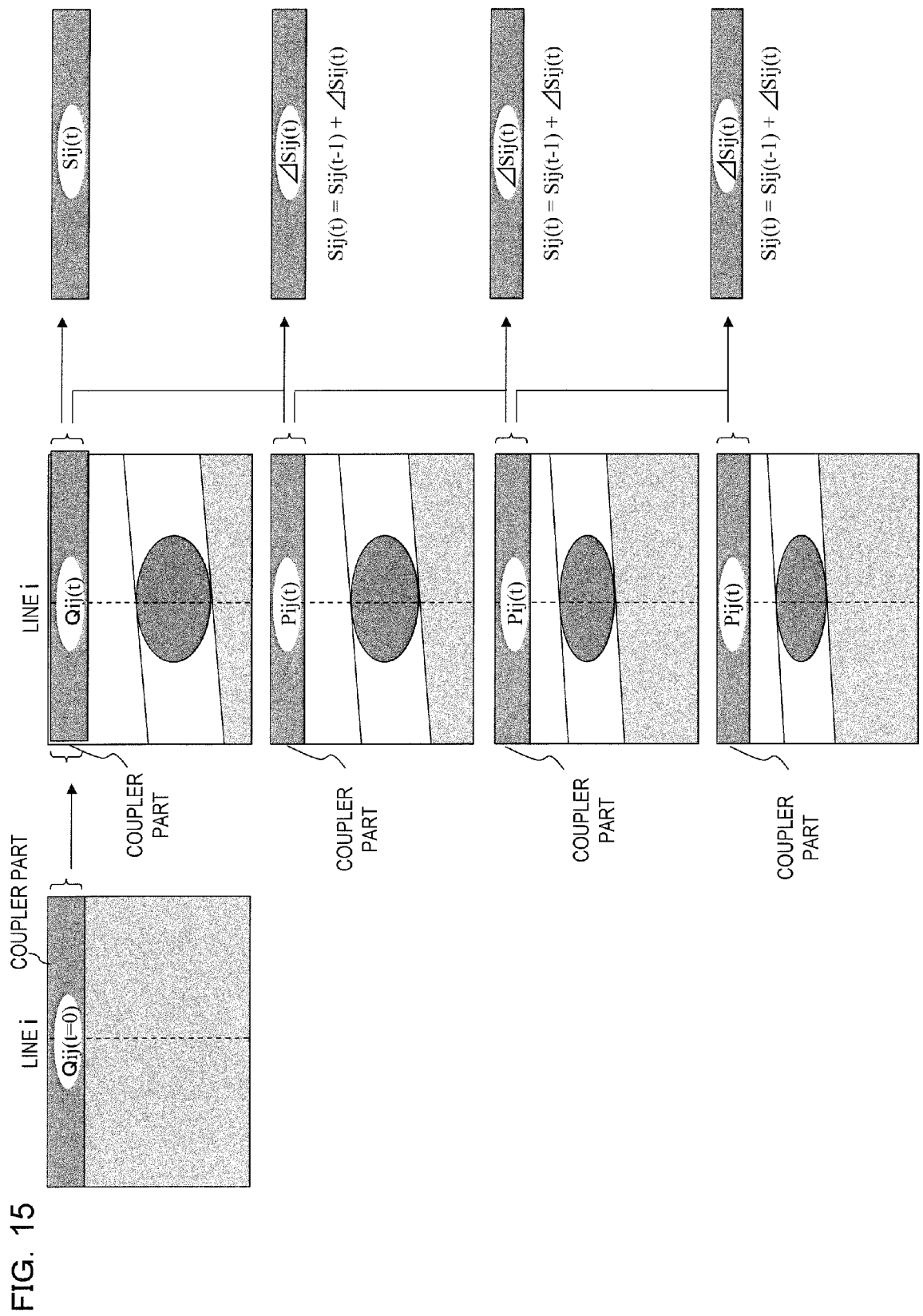
FIG. 15 is a diagram illustrating another example of a process by the coupler pressurization evaluation unit of Example 2.

In Example 3 of the coupler pressurization evaluation, a pair of RF signal frame data obtained at different timings is obtained from the RF signal frame data selection unit 10 continuously at the respective measurement points in time from the initial state to the pressurized state as shown in FIG. 15. Then, the distortion changes ΔSij(t−k), . . . , ΔSij(t) at the respective measurement points i and j are obtained for the entire region in the depth direction of the elastic coupler 20 every time the pair of RF signal frame data is obtained. Subsequently, the distortion change ΔSi, j(t) of timing (t−1) and timing (t), which are temporally adjacent to each other, is obtained as shown in FIG. 15. Furthermore, in regard to a pair of temporally sequential RF signal frame data, the distortion changes ΔSi, j(t−k), . . . , ΔSij(t) are sequentially summed up to obtain the distortion change summed-up value ΣΔSij(t) at the present point in time. Subsequently, ΣΔSij(t) of the measurement points i and j are averaged in the direction of the coordinate j of the coupler echo region to obtain the distortion change summed-up value ΣΔSi*(t) for the measurement point i.

In addition, it is needless to say that Examples 2 and 3 of the coupler pressurization evaluation can be applied to Example 1.

[S16: Conversion Process of Absolute Pressure]

The pressure converter 55 reads the elasticity property (for example, Young's modulus E) corresponding to the ID of the elastic coupler, which has been identified by the coupler ID identification unit 51, from the coupler database 53, uses the average value Si*(t) or the distortion change summed-up value ΣΔSi*(t) input from the coupler pressurization evaluation unit 54, and obtains the absolute pressure distribution Pi(t) by the conversion with the following formulae (5) and (6). In addition, the pressure converter 55 may be integrally formed with the coupler pressurization evaluation unit 54.

$$Pi(t)=Si^*(t) \times E \quad (5)$$

$$Pi(t)=\Sigma \Delta Si^*(t) \times E \quad (6)$$

[S17: Display Process of Pressurizing State]

The process by the pressurizing-state image constructing unit 38 is the same as that in Example 1.

As described above, according to this example, it is possible to accurately measure the absolute pressure applied to the body tissue of the test object 100 by the probe 1 in real time in the test process of the ordinary elasticity image measurement.

In addition, since the ID code of the elastic coupler can be read during the elasticity image measurement process, it is possible to automatically identify the elastic coupler and accurately measure the absolute pressure in accordance with the elasticity property of the elastic coupler even if various different elastic couplers are arbitrarily replaced. Therefore, it is possible to reduce the burden of the operator and thereby to enhance usability.

Although the description was made of the example of the ultrasonic diagnostic apparatus for creating and displaying the elasticity image in Examples 1 and 2, the invention is not limited thereto and can be applied to an ultrasonic diagnostic apparatus for performing tests such as a diagnosis by a tomographic image (B mode image) of the body tissue of the test body, and a bloodstream diagnosis by the Doppler measurement or the color flow mode (CFM). Accordingly, it is possible to accurately execute the evaluation of the pressurized state suitable for various tests.

The invention claimed is:

1. An ultrasonic diagnostic apparatus including an ultrasonic probe configured to transmit and receive ultrasonic waves while in contact with a test body, a transmitting unit configured to transmit the ultrasonic waves to the ultrasonic probe, a receiving unit configured to receive and process an RF signal which is a reflected echo signal received by the ultrasonic probe, an image creating unit configured to create an ultrasonic image based on an RF signal output from the receiving unit, a display unit configured to display the ultrasonic image created by the image creating unit, and a control unit configured to control the transmitting unit and the receiving unit, comprising:

a pressurizing-state evaluation unit configured to evaluate the pressure applied to the test body based on the deformation of an elastic coupler which has been attached to an ultrasonic wave transmitter/receiver surface of the ultrasonic probe, wherein the pressurizing-state evaluation unit includes a coupler attachment detector configured to detect the attachment of the elastic coupler to the ultrasonic wave transmitter/receiver surface of the ultrasonic probe base on an intensity change in the RF signal of the RF signal output from the receiving unit when the intensity change exceeds a pre-set threshold value and configured to detect by generating the multiple echo whether reflected or not, an initialization process unit configured to detect an initial thickness of the elastic coupler in an initial state in which the elastic coupler is not pressurized, by echo detecting the boundary between the elastic coupler and an air, and a coupler pressurization evaluation unit configured to obtain the thickness of the elastic coupler by echo detecting the boundary between the elastic coupler and the test body in a subsequent state in which the elastic coupler is pressurized against the test body, obtaining the thickness change based on the thus obtained thickness and the initial thickness, and evaluating the pressure based on the thickness change and an elasticity property of the elastic coupler.

2. The ultrasonic diagnostic apparatus according to claim 1,
wherein the initialization process unit detects the exposure surface of the elastic coupler based on a time from a point in time at which an ultrasonic signal is output from the transmitting unit to the ultrasonic probe to a point in time at which the intensity of the RF signal corresponding to the ultrasonic signal or the illuminance of the ultrasonic image exceeds a pre-set threshold value for the first time in the state where the elastic coupler is attached, and detects the initial thickness of the elastic coupler.

3. The ultrasonic diagnostic apparatus according to claim 1,
wherein the initialization process unit receives any one of the RF signal and the illuminance data of the ultrasonic image created based on the RF signal, and detects that the elastic coupler has been attached based on a frequency of multiple echo where the intensity of the received RF signal or the illuminance of the ultrasonic image changes so as to exceed the pre-set threshold value.

4. The ultrasonic diagnostic apparatus according to claim 3,
wherein the initialization process unit obtains the initial thickness of the elastic coupler based on the frequency of the multiple echo.

5. The ultrasonic diagnostic apparatus according to claim 1,
wherein the elastic coupler is provided with a layer of ultrasonic scattering bodies formed inside its plate-shaped unit formed from a gel-like material, and
wherein the initialization process unit receives any one of the RF signal and the illuminance data of the ultrasonic image created based on the RF signal, and detects that the elastic coupler has been attached based on an intensity distribution of the received RF signal or an illuminance distribution of the ultrasonic image.

6. The ultrasonic diagnostic apparatus according to claim 1,
wherein the elastic coupler is attached to the ultrasonic probe via an attachment tool,
wherein the attachment tool includes a locking protrusion which is detachably locked in a locking portion formed in a case of the ultrasonic probe, and
wherein the coupler attachment detector detects that the elastic coupler has been attached based on a signal output from an attachment sensor which operates in a state in which the locking protrusion is locked in the locking portion of the ultrasonic probe.

7. The ultrasonic diagnostic apparatus according to claim 5,
wherein the initialization process unit receives any one of the RF signal and the illuminance data of the ultrasonic image created based on the RF signal, detects the exposure surface of the elastic coupler based on the frequency of the multiple echo where the intensity of the received RF signal or the illuminance of the ultrasonic image changes so as to exceed the pre-set threshold value, and detects the initial thickness of the elastic coupler.

8. The ultrasonic diagnostic apparatus according to claim 1,
wherein the coupler pressurization evaluation unit receives any one of the RF signal and the illuminance data of the ultrasonic image created based on the RF signal, and detects that the elastic coupler is in a pressurized state based on the fact that there is no multiple echo where the intensity of the received RF signal or the illuminance of the ultrasonic image periodically changes so as to exceed the pre-set threshold value.

9. The ultrasonic diagnostic apparatus according to claim 1,
wherein the coupler pressurization evaluation unit receives any one of the RF signal corresponding to an ultrasonic signal output from the transmitting unit to the ultrasonic probe and the illuminance data of the ultrasonic image created based on the RF signal, obtains the thickness of the elastic coupler by detecting the boundary between the elastic coupler and the test body based on the time which was required for the intensity of the received RF signal or the illuminance of the ultrasonic image to exceed a pre-set threshold value for the first time, obtains a thickness change by comparing the obtained thickness and the initial thickness, and evaluates an absolute pressure applied to the test body based on the thickness change and an elasticity property of the elastic coupler.

10. The ultrasonic diagnostic apparatus according to claim 1,
wherein the coupler pressurization evaluation unit obtains the thickness of the elastic coupler by detecting the boundary between the elastic coupler and the test body based on the time which was required for the intensity of the RF signal or the illuminance of the ultrasonic image to exceed a pre-set threshold value for the first time, obtains a thickness change rate based on the obtained thickness of the elastic coupler and the initial thickness, and evaluates an absolute pressure applied to the test body based on the change rate and an elasticity property of the elastic coupler.

11. The ultrasonic diagnostic apparatus according to claim 10
wherein the elastic coupler is formed to have a plate-shaped unit from a gel-like material and is obtained by diffusing and mixing ultrasonic scattering bodies inside the plate-shaped unit.

12. The ultrasonic diagnostic apparatus according to claim 1,
wherein the coupler pressurization evaluation unit receives the RF signal frame data output from the receiving unit in an initial state and the RF signal frame data output from the receiving unit in the measurement of a pressurized state, obtains distortion by obtaining displacement of a measurement point within the elastic coupler based on the pair of RF signal frame data, and evaluates the absolute pressure applied to the test body based on the thus obtained distortion and the elasticity property which has been set corresponding to the type of the elastic coupler.

13. The ultrasonic diagnostic apparatus according to claim 1, wherein the coupler pressurization evaluation unit sequentially receives a pair of RF signal frame data which was obtained at different timings and output from the receiving unit while including the initial state, obtains distortions by obtaining displacement of a measurement point within the elastic coupler based on the pair of RF signal frame data, sums up the distortions from the initial state to the pressurized state, and evaluates an absolute pressure applied to the test body based on the distortion summed-up value and the elasticity property.

14. The ultrasonic diagnostic apparatus according to claim 1, wherein the pressurizing-state evaluation unit displays at least one of the numerical value of the obtained absolute pressure, a graph of a temporal change, a bar chart, and the like while aligning or partially overlapping it with the ultrasonic image displayed on the display unit.

15. An ultrasonic diagnostic apparatus including an ultrasonic probe configured to transmit and receive ultrasonic waves while in contact with a test body, a transmitting unit configured to transmit the ultrasonic waves to the ultrasonic probe, a receiving unit configured to receive and process an RF signal which is a reflected echo signal received by the ultrasonic probe, an image creating unit configured to create an ultrasonic image based on a RF signal output from the receiving unit, a display unit configured to display the ultrasonic image created by the image creating unit, and a control unit configured to control the transmitting unit and the receiving unit, comprising:
a pressurizing-state evaluation unit configured to evaluate the pressure applied to the test body based on a compressive deformation of a compressive elastic coupler which has been attached to an ultrasonic wave transmitter/receiver surface of the ultrasonic probe,
wherein the pressurizing-state evaluation unit includes:
a coupler attachment detector configured to detect the attachment of the elastic coupler to the ultrasonic wave transmitter/receiver surface of the ultrasonic probe base on an intensity change in the RF signal of the RF signal output from the receiving unit when the intensity change exceeds a pre-set threshold value and configured to detect by generating the multiple echo whether reflected or not;
an initialization process unit configured to use the reflected echo signal received by the ultrasonic probe to detect an initial thickness of the compressive elastic coupler in an initial state in which the compressive elastic coupler is not compressed, by using the reflected echo signal to detect a boundary between the compressive elastic coupler and an air, to obtain an uncompressed thickness of the compressive elastic coupler, and
a coupler pressurization evaluation unit configured to use the reflected echo signal received by the ultrasonic probe to obtain a compressed thickness of the compressive elastic coupler while the compressive elastic coupler is pressed against the test body, by using the reflected echo signal to detect the boundary between the compressive elastic coupler and the test body, and to obtain a thickness change based on the thus obtained compressed thickness and the uncompressed thickness, and evaluating the pressure based on the thickness change and a compressive elasticity property of the compressive elastic coupler.

16. An ultrasonic diagnostic apparatus including an ultrasonic probe configured to transmit and receive ultrasonic waves while in contact with a test body, a transmitting unit configured to transmit the ultrasonic waves to the ultrasonic probe, a receiving unit configured to receive and process an RF signal which is a reflected echo signal received by the ultrasonic probe, an image creating unit configured to create an ultrasonic image based on a RF signal output from the receiving unit, a display unit configured to display the ultrasonic image created by the image creating unit, and a control unit configured to control the transmitting unit and the receiving unit, comprising:
a pressurizing-state evaluation unit configured to evaluate the pressure applied to the test body based on the deformation of an elastic coupler which has been attached to an ultrasonic wave transmitter/receiver surface of the ultrasonic probe,
wherein the pressurizing-state evaluation unit includes a coupler attachment detector configured to detect the attachment of the elastic coupler to the ultrasonic wave transmitter/receiver surface of the ultrasonic probe base on an intensity change in the RF signal of the RF signal output from the receiving unit when the intensity change exceeds a pre-set threshold value and configured to detect by generating the multiple echo whether reflected or not, an initialization process unit configured to detect an initial thickness of the elastic coupler in an initial state in which the elastic coupler is not pressurized, by echo detecting the boundary between the elastic coupler and an environment, and a coupler pressurization evaluation unit configured to obtain the thickness of the elastic coupler by echo detecting the boundary between the elastic coupler and the test body in a subsequent state in which the elastic coupler is pressurized against the test body, obtaining the thickness change based on the thus obtained thickness and the initial thickness, and evaluating the pressure based on the thickness change and an elasticity property of the elastic coupler.

17. An ultrasonic diagnostic apparatus including an ultrasonic probe configured to transmit and receive ultrasonic waves while in contact with a test body, a transmitting unit configured to transmit the ultrasonic waves to the ultrasonic probe, a receiving unit configured to receive and process an RF signal which is a reflected echo signal received by the ultrasonic probe, an image creating unit configured to create an ultrasonic image based on a RF signal output from the receiving unit, a display unit configured to display the ultrasonic image created by the image creating unit, and a control unit configured to control the transmitting unit and the receiving unit, comprising:
a pressurizing-state evaluation unit configured to evaluate the pressure applied to the test body based on a compressive deformation of a compressive elastic coupler which has been attached to an ultrasonic wave transmitter/receiver surface of the ultrasonic probe,
wherein the pressurizing-state evaluation unit includes:
a coupler attachment detector configured to detect the attachment of the ultrasonic wave transmitter/receiver surface of the ultrasonic probe on an intensity change in the RF signal of the RF signal output from the receiving unit when the intensity change exceeds a pre-set threshold value and configured to detect by generating the multiple echo whether reflected or not;
an initialization process unit configured to use the reflected echo signal received by the ultrasonic probe to detect an initial thickness of the compressive elastic coupler in an initial state in which the compressive elastic coupler is not compressed, by using the reflected echo signal to detect a boundary between the compressive elastic coupler and an environment, to obtain an uncompressed thickness of the compressive elastic coupler, and a coupler pressurization evaluation unit configured to use the reflected echo signal received by the ultrasonic probe to obtain a compressed thickness of the compressive elastic coupler while the compressive elastic coupler is pressed against the test body, by using the reflected echo signal to detect the boundary between the compressive elastic coupler and the test body, and to obtain a thickness change based on the thus obtained compressed thickness and the uncompressed thickness, and evaluating the pressure based on the thickness change and a compressive elasticity property of the compressive elastic coupler.

* * * * *